US012668623B2

(12) United States Patent
Li et al.

(10) Patent No.: US 12,668,623 B2
(45) Date of Patent: Jun. 30, 2026

(54) ANTI-PERIOSTIN HUMANIZED MONOCLONAL ANTIBODY, AND PREPARATION METHOD THEREFOR AND USE THEREOF

(71) Applicant: SHENYANG EYE INDUSTRY TECHNOLOGY INSTITUTE LTD., Liaoning (CN)

(72) Inventors: Xuejiao Li, Liaoning (CN); Wei He, Liaoning (CN); Shuo Zhang, Liaoning (CN); Hang Zhao, Liaoning (CN); Ling Feng, Liaoning (CN); Hui Liu, Liaoning (CN); Hongli Zhao, Liaoning (CN); Xiangdong He, Liaoning (CN)

(73) Assignee: Shenyang Eye Industry Technology Institute Ltd., Liaoning (CN)

( * ) Notice: Subject to any disclaimer, the term of this patent is extended or adjusted under 35 U.S.C. 154(b) by 297 days.

(21) Appl. No.: 18/691,316

(22) PCT Filed: Sep. 9, 2022

(86) PCT No.: PCT/CN2022/118162
§ 371 (c)(1),
(2) Date: Mar. 12, 2024

(87) PCT Pub. No.: WO2023/036305
PCT Pub. Date: Mar. 16, 2023

(65) Prior Publication Data
US 2024/0400658 A1 Dec. 5, 2024

(30) Foreign Application Priority Data

Sep. 13, 2021 (CN) .......................... 202111068177.1

(51) Int. Cl.
C07K 16/18 (2006.01)
G01N 33/577 (2006.01)
A61K 39/00 (2006.01)

(52) U.S. Cl.
CPC .......... *C07K 16/18* (2013.01); *G01N 33/577* (2013.01); *A61K 2039/505* (2013.01); *C07K 2317/24* (2013.01); *C07K 2317/73* (2013.01)

(58) Field of Classification Search
CPC ............... C07K 16/18; C07K 2317/24; C07K 2317/73; C07K 2317/76; G01N 33/577; G01N 33/68; A61K 2039/505; A61P 35/00
USPC ...................................................... 424/133.1
See application file for complete search history.

(56) References Cited

U.S. PATENT DOCUMENTS

| | | | |
|---|---|---|---|
| 2014/0308685 A1 | 10/2014 | Izuhara et al. | |
| 2016/0108109 A1 | 4/2016 | Taniyama et al. | |
| 2020/0239572 A1 | 7/2020 | Baliga et al. | |

FOREIGN PATENT DOCUMENTS

| | | |
|---|---|---|
| CN | 101389656 A | 3/2009 |
| CN | 101888855 A | 11/2010 |
| CN | 103550790 A | 2/2014 |
| CN | 109879963 A | 6/2019 |
| CN | 110551214 A | 12/2019 |
| CN | 111787951 | 10/2020 |
| CN | 114057871 A | 2/2022 |
| EP | 1978034 | 10/2008 |
| EP | 2168599 | 3/2010 |
| JP | WO 2007/077934 | 6/2009 |
| WO | WO 2013/035799 | 3/2013 |
| WO | WO 2014/136910 | 9/2014 |
| WO | WO 2020/121059 | 6/2020 |

OTHER PUBLICATIONS

Li, et al., "Expression and Significance of Periostin and NF-kB in the Tissue of Esophageal Carcinoma," Acta Academiae Medicinae Weifang, Apr. 2014, vol. 36, No. 2, pp. 155-157 (English abstract provided).
Official Action issued in counterpart Chinese Patent Application No. 202280054341.X, mailed Jan. 8, 2025 (English translation provided).
International Search Report and Written Opinion issued in counterpart PCT Application No. PCT/CN2022/118162 dated Oct. 9, 2022 (English translation provided).
Extended European Search Report issued in corresponding European Application No. 22866766.3, dated Sep. 25, 2025.
Ishikawa, K. et al. "Periostin promotes the generation of fibrous membranes in proliferative vitreoretinopathy." *The FASEB Journal*, vol. 28, No. 1, 2013, pp. 131-142.
Naik, Payal K. et al. "Periostin promotes fibrosis and predicts progression in patients with idiopathic pulmonary fibrosis." *Am J Physiol Lung Cell Mol Physiol*, vol. 303, 2012, pp. L1046-L1056.
Taniyama, Yoshiaki et al. "Selective Blockade of Periostin Exon 17 Preserves Cardiac Performance in Acute Myocardial Infarction." *Hypertension*, vol. 67, No. 2, 2015, pp. 356-361.

*Primary Examiner* — Yan Xiao
(74) *Attorney, Agent, or Firm* — Norton Rose Fulbright US LLP

(57) ABSTRACT

Provided in the present application are an anti-periostin humanized monoclonal antibody, and a preparation method therefor and the use thereof. The anti-periostin humanized monoclonal antibody has a relatively high expression level, and also has a better binding specificity and affinity to an antigen.

12 Claims, 17 Drawing Sheets

Specification includes a Sequence Listing.

MW:DL10000
1.9808-2-139-VLA-551-VHB-PEE12.4  OD=1.88    C=1.51ug/ul     total :0.75mg Lane1/2: 9808P-2+551-VHB-139-VLA MW: DL10000                                        Linearized PVUI Control                              periositin periostin+IgG                        periostin+Postn nAb

RPE-19

Control                    periositin periostin+IgG              periostin+Postn nAb

RPE-19

ANTI-PERIOSTIN HUMANIZED MONOCLONAL ANTIBODY, AND PREPARATION METHOD THEREFOR AND USE THEREOF

CROSS REFERENCE TO RELATED APPLICATIONS

This application is a U.S. National Phase application under 35 U.S.C. § 371 of PCT Application No. PCT/CN2022/118162 filed Sep. 9, 2022, which claims the priority of Chinese Patent Application No. 202111068177.1, filed with the China National Intellectual Property Administration on Sep. 13, 2021, and titled with "anti-periostin humanized monoclonal antibody, and preparation method therefor and use thereof", the disclosure of which is hereby incorporated by reference in its entirety.

INCORPORATION OF SEQUENCE LISTING

The instant application contains a Sequence Listing which has been submitted in XML format and is hereby incorporated by reference in its entirety. Said XML copy, created on Mar. 12, 2024, is named UNITP0025US_Corrected_Sequence_Listing and is 53,972 bytes in size.

FIELD

The present invention relates to the technical field of antibody drugs, and particularly relates to a humanized anti-periostin monoclonal antibody, and preparation method therefor and use thereof.

BACKGROUND

Currently, vitreoretinal diseases such as proliferative diabetic retinopathy (PDR), proliferative vitreoretinopathy (PVR) and age-related macular degeneration (AMD) are the leading cause of vision impairment and vision loss in the corresponding population, and are also a medical problem worldwide. Therefore, it is necessary to find a novel biological label and therapeutic target for vitreoretinal diseases, which is essential for early detection, diagnosis, and treatment of these diseases.

Periostin is a cell adhesion protein found in mouse embryo osteoblast precursor cells in 1993 and named osteoblast-specific factor-2 (OSF-2). Due to its specifical expression in the periodontium and periosteum of adult mice, it is renamed periostin. Periostin is a unique extracellular matrix protein, which is involved in the immune-inflammatory responses corresponding to various tissues and organs of the human body, such as cardiac remodelling after myocardial infarction, myelofibrosis, regeneration and repair of periodontal tissues, cutaneous wound healing, tumor cell metastasis and renal injury, and induces chronic allergic diseases. In recent years, the research and production of periostin-targeted drugs has become a hotspot, and a large number of marketed drugs have achieved impressive success in tumor therapy.

The main roles of periostin in the eye include promoting cell proliferation, differentiation, migration and adhesion, inducing fiber formation and promoting neovascularization. It has been proved that periostin is a key factor in various vitreoretinal diseases in more and more domestic and international studies. Periostin is expected as a new biological label for vitreoretinal diseases, which will provide a new therapeutic strategy. For example, in many fields of ophthalmology, the periostin antibody has been reported to play a key role in the treatment of intraocular neovascular proliferation and macular oedema, etc., caused by age-related macular degeneration and diabetic retinopathy.

However, all existing periostin antibodies are murine monoclonal antibodies. As the murine antibodies are heterologous proteins, they may cause immune rejection against the heterologous proteins and induce the production of human anti-mouse antibodies in the human body, which shortens the half-life of the antibodies in vivo and impairs the therapeutic efficacy. Therefore, it is desirable to conduct antibody humanization on periostin antibody while maintaining a high affinity for specific antigenic epitopes to reduce the immunogenicity of the heterologous antibody and improve the specificity and affinity of binding to the antigen, leading to better therapeutic effects.

SUMMARY

In view of this, the present invention aims to provide a humanized anti-periostin monoclonal antibody, preparation method and use thereof.

A humanized anti-periostin monoclonal antibody provided by the present invention comprises a heavy chain variable region and a light chain variable region, wherein the heavy chain variable region comprises an amino acid sequence set forth in SEQ ID NO: 1, and the light chain variable region comprises an amino acid sequence set forth in SEQ ID NO: 2.

The humanized anti-periostin monoclonal antibody provided by the present invention comprises a heavy chain constant region and a light chain constant region, wherein the heavy chain constant region is a heavy chain constant region of human IgG1, and the light chain constant region is a light chain constant region of kappa chain.

In some specific embodiments, the humanized anti-periostin monoclonal antibody comprises a heavy chain and a light chain, wherein the amino acid sequence of the heavy chain is set forth in SEQ ID NO: 3, and the amino acid sequence of the light chain is set forth in SEQ ID NO: 4.

In the present invention, antibody humanization is performed on a murine anti-periostin monoclonal antibody, and a eukaryotic expression vector is successfully constructed and transfected into mammalian CHO cells for expression and secretion. The biological functions such as affinity and binding activity are evaluated in vitro by SDS-PAGE, ELISA, WB, etc., which provides a theoretical basis for the large-scale expression of the humanized anti-periostin monoclonal antibody in CHO cells.

The anti-periostin humanized monoclonal antibody provided by the present invention comprises the above-mentioned heavy chain and light chain, which functions more safely and effectively than chimeric antibodies or other murine periostin monoclonal antibodies produced in the art. The humanized antibodies have been tested and shown to have good specificity against human periostin. It is confirmed that the periostin antibody plays a key role in the treatment of diseases such as intraocular neovascular proliferation and macular edema which are caused by age-related macular degeneration and diabetic retinopathy in many fields of ophthalmology, so the antibody provided by the present invention has the potential to treat tissue fibrosis.

The present invention further provides a nucleic acid encoding the anti-periostin humanized monoclonal antibody. Specifically, the present invention provides a nucleic acid encoding the heavy chain of said monoclonal antibody, a nucleic acid encoding the light chain of said monoclonal antibody, a nucleic acid encoding the heavy chain variable region of said monoclonal antibody, and/or a nucleic acid encoding the light chain variable region of said monoclonal antibody. In some embodiments, the nucleic acid encoding heavy chain of said antibody is set forth in SEQ ID NO: 5, and the nucleic acid encoding the light chain of said antibody is set forth in SEQ ID NO: 6. In order to facilitate protein expression, the 5' end of the coding nucleic acid provided by the present invention further comprises a linker. Thus, in some specific embodiments, the nucleic acid encoding the heavy chain of the humanized anti-periostin monoclonal antibody is set forth in SEQ ID NO: 7; and the nucleic acid encoding the light chain of the humanized anti-periostin monoclonal antibody is set forth in SEQ ID NO: 8.

The present invention further provides an expression vector which comprises the nucleic acid encoding said monoclonal antibody. In the present invention, the expression vector comprises a backbone vector. In some embodiments, the backbone vector is pCDNA3.4.

The present invention further provides a host cell transformed or transfected with the expression vector. In the present invention, the host cell is a mammalian cell, and in some specific embodiments, the host cell is a CHO-K1 cell.

A method for producing the humanized anti-periostin monoclonal antibody of the present invention comprises culturing the host cell of the present invention and inducing the expression of the humanized anti-periostin monoclonal antibody.

The present invention further provides use of the humanized anti-periostin monoclonal antibody in the manufacture of a drug or a detection reagent, wherein the drug is a medicament for the treatment of tissue fibrosis and/or a malignant tumor, and the detection reagent is for diagnosing tissue fibrosis and/or a malignant tumor. In some embodiments, the tissue fibrosis is retinal fibrosis.

The present invention further provides a drug, which comprises the humanized anti-periostin monoclonal antibody of the present invention.

The present invention further provides a kit, which comprises the humanized anti-periostin monoclonal antibody, a composition formed by combining this antibody with a chemical label or a biological label, and a conjugate formed by coupling the humanized anti-periostin monoclonal antibody with a solid medium or a semi-solid medium.

In the present invention, the chemical label is isotopes, immunotoxins and/or chemical drugs and the biological label is biotin, affinities or enzyme labels. The enzyme label is preferably horseradish peroxidase or alkaline phosphatase. The immunotoxin is preferably aflatoxin, diphtheria toxin, *Pseudomonas aeruginosa* exotoxin, ricin, abrin, mistletoe lectin, modeccin, PAP, saporin, gelonin, or luffin. The solid medium or non-solid medium in the conjugate is selected from the group consisting of colloidal gold, polystyrene plates and beads. This kit can be used for diagnosing tissue fibrosis and/or a malignant tumor. The method for diagnosing employs the immunological detection techniques such as ELISA, Western blot, immunofluorescence techniques and immunohistochemistry assays.

The present invention further provides a method for the treatment of tissue fibrosis and/or a malignant tumor, which comprises administering the drug of the present invention.

The present invention further provides a method for diagnosing tissue fibrosis and/or a malignant tumor, in which the diagnosis is carried out by using the detection reagent of the present invention.

The present invention provides a humanized anti-periostin monoclonal antibody, in which only the complementary determining regions of the variable region from the murine McAb is retained, which bind to the antigen, and CDR grafting antibodies are produced. The humanized anti-periostin monoclonal antibodies have less immunogenicity compared to chimeric antibodies. In the experiments of the present invention, the obtained antibody could be produced in higher level, shows better specificity and affinity for binding to antigen compared to other antibodies, and involves in human immune response more effectively.

BRIEF DESCRIPTION OF DRAWINGS

FIGS. 3-1 and 3-2 show plasmid profiles containing heavy and light chains, respectively.

DETAILED DESCRIPTION

The present invention provides a humanized anti-periostin monoclonal antibody, preparation method and use thereof. Those skilled in the art can learn from the contents of the disclosure and appropriately adapt the process parameters to achieve the disclosure. It should be noted that all similar replacements and modifications are obvious to those skilled in the art, and they are deemed to be included in the present invention. The method and use of the present invention have been described through preferred embodiments, and those skilled apparently can make modifications or appropriate changes and combinations of the method and use herein without departing from the content, spirit and scope of the present invention to realize and apply the technology of the present invention.

Unless defined otherwise, all technical and scientific terms used herein have the same meaning as understood by those ordinarily skilled in the art. For definitions and terms in the art, professionals can in particular refer to Current Protocols in Molecular Biology (Ausubel). The abbreviations for amino acid residues are the standard 3-letter and/or 1-letter codes used in the art to refer to one of the 20 commonly used L-amino acids.

The term "antibody" refers to a protein consisting of one or more polypeptides that bind specifically to an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions. The term "monoclonal antibody" refers to a preparation of an antibody molecule consisting of a single molecule. The monoclonal antibody composition shows a single binding specificity and affinity for a specific epitope.

The "variable region" of a heavy or light chain of an antibody is the N-terminal mature region of the chain. Currently known antibody include kappa and lambda light chains, and the alpha, gamma (IgG1, IgG2, IgG3, IgG4), delta, epsilon and mu heavy chains or equivalents in other species. Full-length immunoglobulin "light chains" (of about 25 kDa or about 214 amino acids) comprise a variable region of about 110 amino acids at the NH2-terminus and a kappa or lambda constant region at the COOH-terminus. Full-length immunoglobulin "heavy chains" (of about 50 kDa or about 446 amino acids), similarly comprise a variable region (of about 116 amino acids) and one of the heavy chain constant regions, e.g., gamma (of about 330 amino acids).

Figure 1:
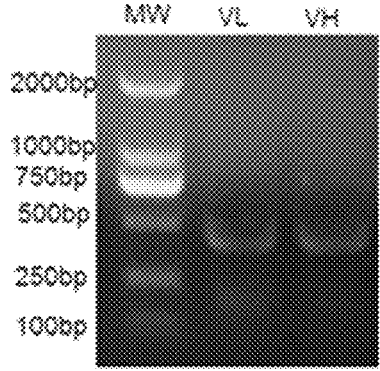
FIG. 1 shows the results for amplification of VH and VL gene derived from murine hybridoma cells (45-2-G3-1-G7-B7) by PCR.

The terms "antibodies" include antibodies or immunoglobulins of any isotype and fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. Provided by the present invention is a humanized anti-periostin monoclonal antibody. Total RNA is extracted from the cultured hybridoma cell 45-2-G3-1-G7-B7. The cDNA is synthesized by reverse transcription using oligonucleotide primers, VH and VL fragments are amplified using IgG degenerate primers and kappa-specific primers, respectively, and the results are observed by gel electrophoresis (FIG. 1). Then, the PCR products are subcloned into standard vectors for clone picking and PCR verification (FIG. 2) and positive clones are sequenced. In order to construct the complete gene encoding the humanized anti-periostin monoclonal antibody and an eukaryotic expression vector containing this complete gene, the gene synthesis is used for replacing the gene encoding the framework region in the variable region of the murine anti-periostin monoclonal antibody with that of the human antibody, and recombining the gene fragment encoding the variable region of the humanized antibody into the vector containing the regulatory sequences and the gene encoding the human constant region. The expression vector is transfected into the CHO-K1 cells. CHO-K1 cell line that continuously and stably secretes the humanized antibody is obtained by screening with the GS system.

The amino acid sequence of the heavy chain variable region of the humanized anti-periostin monoclonal antibody of the present invention is

```
                                    (SEQ ID NO: 1)
EVQLVQSGAEVKKPGESLKISCKASGYSFTDYFMNWVRQMPGKGLEWIGR

INPYSGDTLYNQRLQGQVTLSADKSISTAYLQLSSLKASDTAMYYCGRSG

VSGLDYWGQGTLVTVSS.
```

The amino acid sequence of the light chain variable region of the humanized anti-periostin monoclonal antibody of the present invention is

```
                                    (SEQ ID NO: 2)
DIQLTQSPSSLSASVGDRVTITCSASSSASYMHWYQQKPGKAPKNWIYDT

SKLASGVPSRFSGSGSGTDYTLTISSLQPEDAATYYCQQWSSNPPTFGGG

TKVEIK.
```

The amino acid sequence of the heavy chain constant region of the humanized anti-periostin monoclonal antibody of the present invention is

```
                                    (SEQ ID NO: 9)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK.
```

The amino acid sequence of the light chain constant variable region of the humanized anti-periostin monoclonal antibody of the present invention is

```
                                   (SEQ ID NO: 10)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC.
```

The amino acid sequence of the heavy chain of the humanized anti-periostin monoclonal antibody of the present invention is (SEQ ID NO: 3)
```
MKHLWFFLLLVAAPRWVLSEVQLVQSGAEVKKPGESLKISCKASGYSFTD

YFMNWVRQMPGKGLEWIGRINPYSGDTLYNQRLQGQVTLSADKSISTAYL

QLSSLKASDTAMYYCGRSGVSGLDYWGQGTLVTVSSASTKGPSVFPLAPS

SKSTSGGTAALGCLVKDYFPEPVTVSWNSGALTSGVHTFPAVLQSSGLYS

LSSVVTVPSSSLGTQTYICNVNHKPSNTKVDKKVEPKSCDKTHTCPPCPA

PELLGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKALPAP

IEKTISKAKGQPREPQVYTLPPSREEMTKNQVSLTCLVKGFYPSDIAVEW

ESNGQPENNYKTTPPVLDSDGSFFLYSKLTVDKSRWQQGNVFSCSVMHEA

LHNHYTQKSLSLSPGK.
```

The amino acid sequence of the light chain of the humanized anti-periostin monoclonal antibody of the present invention is (SEQ ID NO: 4)
```
MVLQTQVFISLLLWISGAYGDIQLTQSPSSLSASVGDRVTITCSASSSAS

YMHWYQQKPGKAPKNWIYDTSKLASGVPSRFSGSGSGTDYTLTISSLQPE

DAATYYCQQWSSNPPTFGGGTKVEIKRTVAAPSVFIFPPSDEQLKSGTAS

VVCLLNNFYPREAKVQWKVDNALQSGNSQESVTEQDSKDSTYSLSSTLTL

SKADYEKHKVYACEVTHQGLSSPVTKSFNRGEC.
```

To facilitate the expression and purification of the antibodies, a linker is added to the N-terminus of the heavy-chain and light-chain fragment during vector construction and protein expression. This linker is removed during subsequent purification. In some embodiments, the amino acid sequence of the linker added at the N-terminus of the heavy chain of the humanized anti-periostin monoclonal antibody is MKHLWFFLLLLVAAPRWVLS (SEQ ID NO: 11) and the amino acid sequence of the linker added at the N-terminus of the light chain of the humanized anti-periostin monoclonal antibody is MVLQTQVFISLLLWISGAYG (SEQ ID NO: 12).

Antibodies may be labeled for detection, for example, antibodies may be labeled and detected by using radioisotopes, enzymes that produce detectable substances, fluorescent proteins, biotin, and the like. Antibodies may also be bound to solid phase carriers including, but not limited to, polystyrene plates, beads, and the like.

The drug of the present invention comprises at least one pharmaceutical active ingredient, further comprising a pharmaceutically acceptable carrier. Preferably, the pharmaceutically acceptable carrier is water, buffered aqueous solution, isotonic salt solution such as PBS (phosphate buffer solution), glucose, mannitol, dextrose, lactose, starch, magnesium stearate, cellulose, magnesium carbonate, 0.3% glycerol, hyaluronic acid, ethanol and polyalkylene glycol such as polypropylene glycol, triglycerides and the like. The type of pharmaceutically acceptable carrier used is depends in particular on whether the composition of the present invention is to be administered orally, nasally, intradermally, subcutaneously, intramuscularly or intravenously. The composition according to the present invention may comprise wetting agents, emulsifiers or buffer substances as additives.

The reagents materials used in the present invention are all commercially available. The present invention is further described below in combination with examples.

Example 1

1. Antibody Humanization Design
(1) Verification of CDR Sequences
Total mRNA was extracted from murine hybridoma cells (45-2-G3-1-G7-B7, for the construction method, see "Chimeric anti-human periostin monoclonal antibody and use thereof", application No. 202010788885.1, from Shenyang He's Eye Industry Group Co., Ltd./Shenyang Eye Industry Technology Research Institute Co., Ltd.) and used as a template for cDNA synthesis. The two DNA fragments encoding the heavy chain variable region and the light chain variable region were separated from the cDNA, cloned into the vector and sequenced. The following amino acid sequences were obtained:

```
>45-2-G3-1-G7-B7-VL1
                                    (SEQ ID NO: 13)
DIVLTQSPAIMSASPGDKVTMTCSASSSASYMHWYQQKSGTSPKRWIYDT

SKLASGVPARFSGSGSGTSYSLTISSMEAEDAATYYCQQWSSNPPTFGGG

TKLEIK
```

```
>45-2-G3-1-G7-B7-VL2 and VL3
                                    (SEQ ID NO: 14)
QIVLTQSPVIMSASPGDKVTMTCSASSSASYMHWYQQKSGTSPKRWIYDT

SKLASGVPARFSGSGSGTSYSLTISSMEAEDAATYYCQQWSSNPPTFGGG

TKLEIK
```

```
>45-2-G3-1-G7-B7-VH
                                    (SEQ ID NO: 15)
EVQLQQSGPELVKPGASVRISCKASGYSFTDYFMNWVKQSHGRSLEWIGR

INPYSGDTLYNQRLKGKATLTVDKSSSTAHMELLSLTSEDSAVYYCGRSG

VSGLDYWGQGTSVTVSS
```

The amino acid sequences of the 3 CDRs in the light chain variable region are sequentially SSASY (SEQ ID NO: 16), DTS, and QQWSSNPPT (SEQ ID NO: 17).

The amino acid sequences of the 3 CDRs in the heavy chain variable region are sequentially GYSFTDYF (SEQ ID NO: 18), INPYSGDT (SEQ ID NO: 19) and GRSGVSGLDY (SEQ ID NO: 20).

(2) Sequence Alignment and CDR Grafting of Murine Antibody
The sequences of the mouse antibody variable region were entered and searched in the IMGT mouse and human V genome databases using Igblast developed by NCBI. Sequence alignment was conducted to determine the human antibody variable region with the highest homology, and then the mouse antibody CDRs were grafted onto the human acceptor framework region to complete the CDR grafting.

Figure 2:
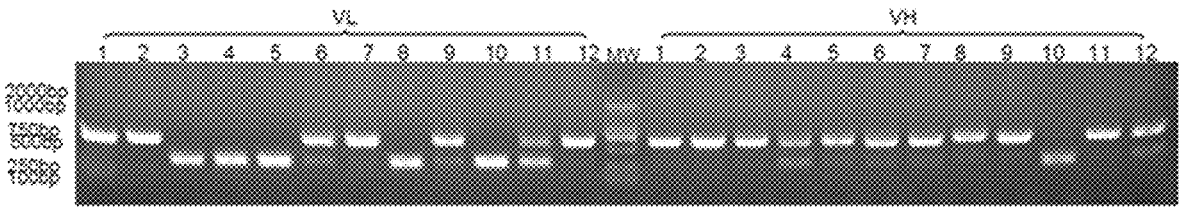
FIG. 2 shows the PCR results after cloning.
Figures 1, 3:
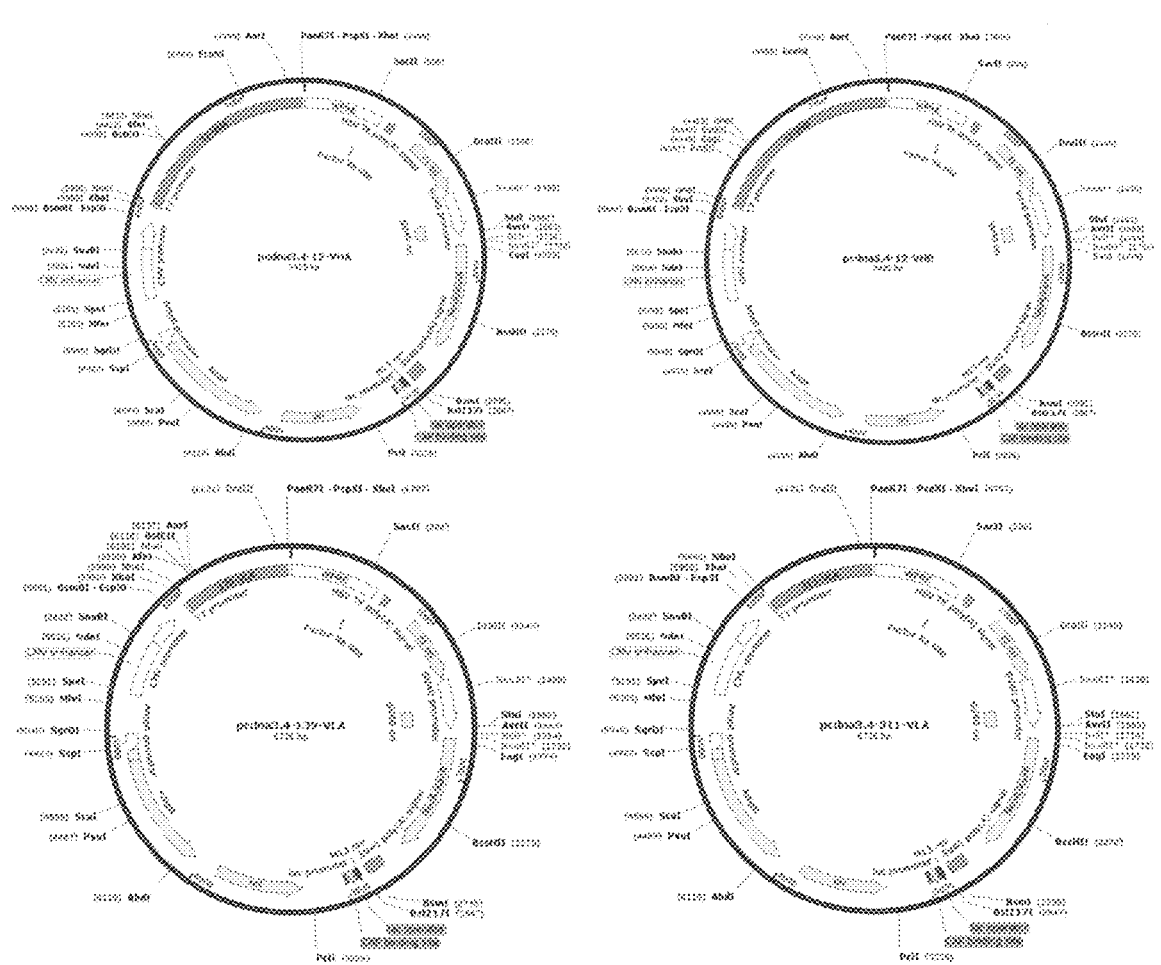
Figures 2, 3:
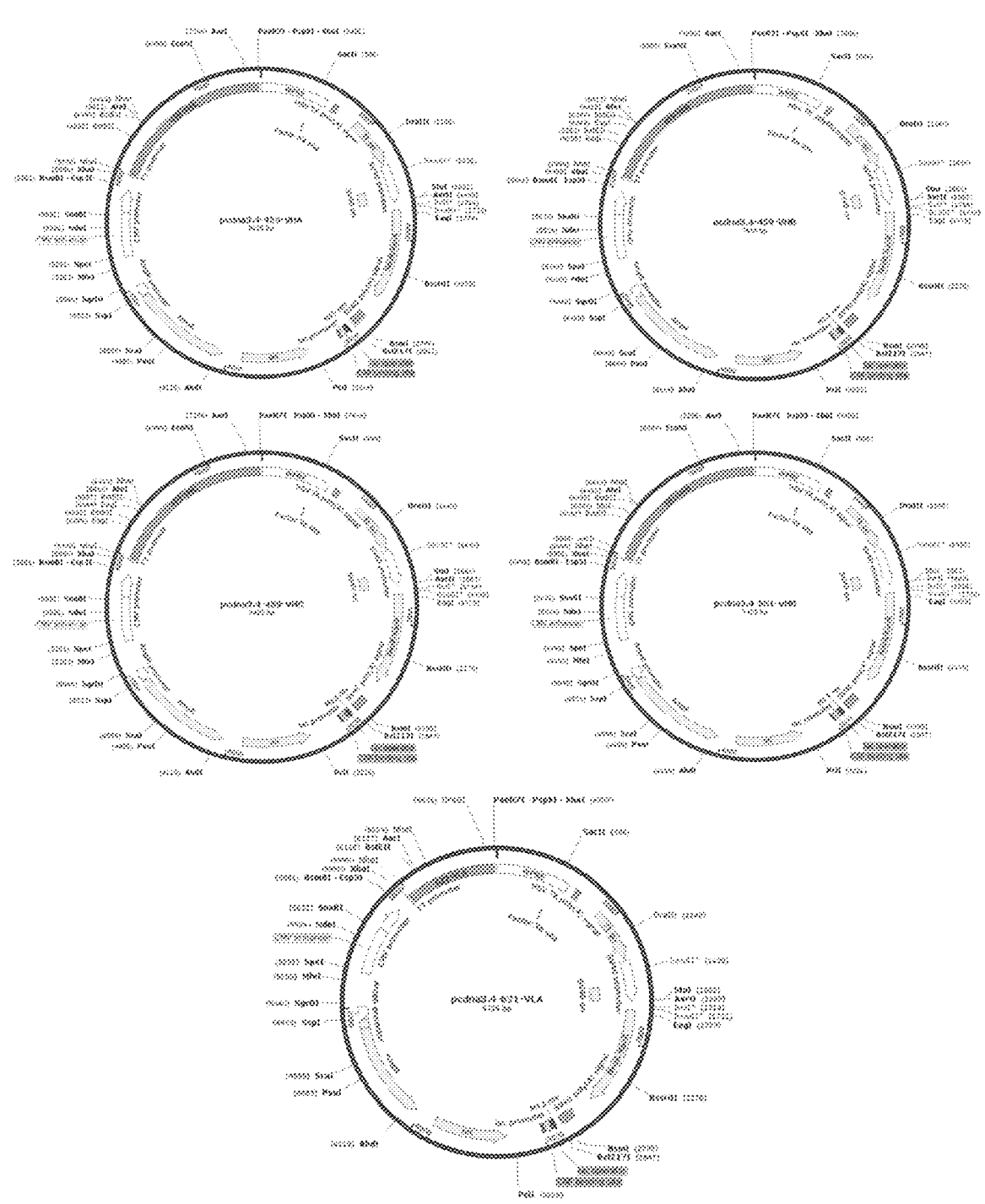

2. Vector Construction and Expression for 18 Humanized Antibodies
(1) Gene Synthesis
The DNA sequence of variable region was linked to that of human constant region and inserted human expression vector pcDNA3.4. The plasmid profiles are shown in FIG. 3-1 and FIG. 3-2. The nucleic acid sequences and amino acid sequences of the heavy chain and light chain of periostin antibody are as follows.

(2) Subcloning into Expression Vector

After gene synthesis, codon optimization was carried out for CHO system and the plasmid was subcloned into the PATX1 expression vector.

The nucleic acid sequences:

---

DNA sequence

---

>12-VHA-1423 bp (SEQ ID NO: 21)

```
gaattcgccgccaccATGAAGCACCTGTGGTTTTTCCTGCTGCTGGTGGCCGCCCCCAGG
TGGGTTCTGTCCCAGGTGCAGCTGGTGCAGAGCGGCGCCGAGGTGAAGAAGCCTGG
CGCTTCCGTGAAGGTGTCCTGCAAGGCTTCTGGCTATAGCTTTACCGATTATTTCATGA
ACTGGGTGCGGCAGGCTCCTGGCCAGGGCTTGGAGTGGATCGGCAGGATCAACCCTT
ACTCCGGCGACACCCTGTATAACCAGAGGCTGAAGGGCCGGGCCACCCTGACCGTGG
ATAAGAGCATCAGCACCGCTTATATGGAGCTGTCCCGGCTGCGGTCCGACGACACCGC
TGTGTATTACTGCGGCAGGTCCGGCGTGTCCGGCCTGGATTACTGGGGCCAGGGCACC
CTGGTGACCGTGAGCAGCgctagcACCAAGGGACCTTCTGTGTTCCCTCTGGCTCCTTCT
TCTAAGTCCACTTCCGGTGGTACAGCAGCTCTGGGTTGTCTGGTGAAGGATTACTTCC
CAGAACCAGTGACTGTGTCCTGGAACTCCGGAGCTCTGACTTCTGGAGTGCATACTTT
CCCAGCAGTGCTGCAATCTAGCGGACTGTACTCTCTGTCTTCCGTGGTGACTGTGCCT
TCTTCTTCCCTGGGGACTCAAACTTACATCTGCAACGTGAACCACAAGCCCTCCAACA
CCAAGGTGGACAAGAAGGTGGAGCCAAAGAGCTGCGATAAGACCCACACCTGTCCA
CCTTGTCCAGCTCCAGAACTGCTGGGTGGGCCTTCTGTGTTTCTGTTCCCACCTAAGC
CAAAGGATACCCTGATGATCTCTAGGACCCCAGAAGTGACCTGTGTGGTCGTCGATGT
GTCTCATGAAGACCCTGAAGTGAAGTTCAACTGGTACGTGGACGGGGTGGAAGTGCA
TAACGCAAAGACCAAGCCCAGGGAAGAGCAATACAACTCCACCTACAGGGTGGTCTC
CGTCCTGACAGTCCTGCATCAGGATTGGCTGAACGGCAAGGAGTACAAGTGCAAGGT
CTCCAATAAAGCCCTGCCTGCCCCTATCGAGAAAACCATTAGCAAAGCCAAAGGCCA
GCCCAGGGAGCCCCAGGTCTATACACTGCCCCCCAGCAGGGAGGAGATGACAAAAA
TCAGGTCAGCCTGACATGCCTGGTCAAAGGCTTTTATCCCAGCGACATTGCCGTCGAG
TGGGAGTCCAATGGCCAGCCCGAGAATAATTATAAAACAACACCCCCCGTCCTGGACA
GCGACGGCAGCTTTTTTCTGTATAGCAAACTGACAGTCGATAAAAGCAGGTGGCAGC
AGGGCAATGTCTTTTTCCTGCAGCGTCATGCACGAGGCCCTGCACAATCACTATACTCA
GAAAAGCCTGAGCCTGTCCCCCGGGAAATGAGCGGCCGC
```

>12-VHB-1423 bp (SEQ ID NO: 22)

```
gaattcgccgccaccATGAAGCACCTGTGGTTTTTCCTGCTGCTGGTGGCCGCTCCTCGGT
GGGTGCTGTCCCAGGTGCAGCTGGTGCAGAGCGGCGCCGAGGTGAAGAAGCCTGGC
GCTTCCGTGAAGGTGTCCTGTAAGGCCAGCGGCTACAGCTTCACCGACTACTTTATGA
ACTGGGTGAGGCAGGCTCCTGGCCAGGGCCTGGAGTGGATCGGCAGGATCAACCCCT
ATAGCGGCGACACCCTGTACAATCAGAAGCTGCAGGGCCGGGTGACCATGACCGTGG
ACAAGTCCATCAGCACCGCTTACATGGAGCTGTCCCGGCTGCGGAGCGACGATACCG
CTGTGTATTACTGCGGCCGGTCCGGCGTGAGCGGCTTGGATTATTGGGGCCAGGGCAC
CCTGGTGACCGTGAGCTCCgctagcACCAAGGGACCTTCTGTGTTCCCTCTGGCTCCTTC
TTCTAAGTCCACTTCCGGTGGTACAGCAGCTCTGGGTTGTCTGGTGAAGGATTACTTC
CCAGAACCAGTGACTGTGTCCTGGAACTCCGGAGCTCTGACTTCTGGAGTGCATACTT
TCCCAGCAGTGCTGCAATCTAGCGGACTGTACTCTCTGTCTTCCGTGGTGACTGTGCC
TTCTTCTTCCCTGGGGACTCAAACTTACATCTGCAACGTGAACCACAAGCCCTCCAAC
ACCAAGGTGGACAAGAAGGTGGAGCCAAAGAGCTGCGATAAGACCCACACCTGTCC
ACCTTGTCCAGCTCCAGAACTGCTGGGTGGGCCTTCTGTGTTTCTGTTCCCACCTAAG
CCAAAGGATACCCTGATGATCTCTAGGACCCCAGAAGTGACCTGTGTGGTCGTCGATG
TGTCTCATGAAGACCCTGAAGTGAAGTTCAACTGGTACGTGGACGGGGTGGAAGTGC
ATAACGCAAAGACCAAGCCCAGGGAAGAGCAATACAACTCCACCTACAGGGTGGTCT
CCGTCCTGACAGTCCTGCATCAGGATTGGCTGAACGGCAAGGAGTACAAGTGCAAGG
TCTCCAATAAAGCCCTGCCTGCCCCTATCGAGAAAACCATTAGCAAAGCCAAAGGCCA
GCCCAGGGAGCCCCAGGTCTATACACTGCCCCCCAGCAGGGAGGAGATGACAAAAAA
TCAGGTCAGCCTGACATGCCTGGTCAAAGGCTTTTATCCCAGCGACATTGCCGTCGAG
TGGGAGTCCAATGGCCAGCCCGAGAATAATTATAAAACAACACCCCCCGTCCTGGACA
GCGACGGCAGCTTTTTTCTGTATAGCAAACTGACAGTCGATAAAAGCAGGTGGCAGC
AGGGCAATGTCTTTTTCCTGCAGCGTCATGCACGAGGCCCTGCACAATCACTATACTCA
GAAAAGCCTGAGCCTGTCCCCCGGGAAATGAGCGGCCGC
```

>459-VHA-1423 bp (SEQ ID NO: 23)

```
gaattcgccgccaccATGAAGCACCTGTGGTTTTTCCTGCTGCTGGTGGCCGCCCCCGGTGG
GTGCTGTCCCAGGTGCAGCTGCAGGAGAGCGGCCCTGGCCTGGTGAAGCCCAGCGA
GACCCTGAGCCTGACCTGCACCGCTTCCGGCTACAGCTTCACCGATTACTTCATGAAC
TGGGTGCGGCAGCCCCTGGCAAGGGCTTGGAGTGGATCGGCAGGATCAACCCTTAC
AGCGGCGACACCCTGTATAATCAGCGGCTGAAGGGCAGGGTGACCCTGAGCGTGGAT
AAGAGCAAGAACCAGGCCAGCCTGAAGCTGAGCAGCGTGACCGCTGCCGATACCGC
CGTGTATTATTGTGGCCGGTCCGGCGTGAGCGGCCTGGATTACTGGGGCCAGGGCACC
CTGGTGACCGTGAGCAGCgctagcACCAAGGGACCTTCTGTGTTCCCTCTGGCTCCTTCT
TCTAAGTCCACTTCCGGTGGTACAGCAGCTCTGGGTTGTCTGGTGAAGGATTACTTCC
CAGAACCAGTGACTGTGTCCTGGAACTCCGGAGCTCTGACTTCTGGAGTGCATACTTT
CCCAGCAGTGCTGCAATCTAGCGGACTGTACTCTCTGTCTTCCGTGGTGACTGTGCCT
TCTTCTTCCCTGGGGACTCAAACTTACATCTGCAACGTGAACCACAAGCCCTCCAACA
CCAAGGTGGACAAGAAGGTGGAGCCAAAGAGCTGCGATAAGACCCACACCTGTCCA
CCTTGTCCAGCTCCAGAACTGCTGGGTGGGCCTTCTGTGTTTCTGTTCCCACCTAAGC
```

-continued

| DNA sequence |
| --- |

```
CAAAGGATACCCTGATGATCTCTAGGACCCCAGAAGTGACCTGTGTGGTCGTCGATGT
GTCTCATGAAGACCCTGAAGTGAAGTTCAACTGGTACGTGGACGGGGTGGAAGTGCA
TAACGCAAAGACCAAGCCCAGGGAAGAGCAATACAACTCCACCTACAGGGTGGTCTC
CGTCCTGACAGTCCTGCATCAGGATTGGCTGAACGGCAAGGAGTACAAGTGCAAGGT
CTCCAATAAAGCCCTGCCTGCCCCTATCGAGAAAACCATTAGCAAAGCCAAAGGCCA
GCCCAGGGAGCCCCAGGTCTATACACTGCCCCCCAGCAGGGAGGAGATGACAAAAAA
TCAGGTCAGCCTGACATGCCTGGTCAAAGGCTTTTATCCCAGCGACATTGCCGTCGAG
TGGGAGTCCAATGGCCAGCCCGAGAATAATTATAAAACAACACCCCCCGTCCTGGACA
GCGACGGCAGCTTTTTTCTGTATAGCAAACTGACAGTCGATAAAAGCAGGTGGCAGC
AGGGCAATGTCTTTTCCTGCAGCGTCATGCACGAGGCCCTGCACAATCACTATACTCA
GAAAAGCCTGAGCCTGTCCCCCGGGAAATGAGCGGCCGC
```

>459-VHB-1423 bp (SEQ ID NO: 24)
```
gaattcgccgccaccATGAAGCACCTGTGGTTTTTCCTGCTGCTGGTGGCTGCTCCTCGGT
GGGTGCTGAGCCAGGTGCAGCTGCAGGAGAGCGGCCCCGGACTGGTGAAGCCTAGC
GAGACCCTGTCCCTGACCTGCACCGCCAGCGGCTATTCCTTTACCGATTATTTCATGAA
CTGGATCCGGCAGCCCCCTGGCAAGGGCCTGGAGTGGATCGGCCGGATCAACCCCTA
TTCCGGCGATACCCTGTACAACCAGCGGCTGAAGTCCAGGGTGACCCTGAGCGTGGA
CAAGTCCAAGAACCAGGCTTCCCTGAAGCTGTCCAGCGTGACCGCTGCTGATACCGC
TGTGTACTACTGCGCCGGGAGCGGCGTGTCCGGCTTGGATTATTGGGGCCAGGGCACC
CTGGTGACCGTGAGCAGCgctagcACCAAGGGACCTTCTGTGTTCCCTCTGGCTCCTTCT
TCTAAGTCCACTTCCGGTGGTACAGCAGCTCTGGGTTGTCTGGTGAAGGATTACTTCC
CAGAACCAGTGACTGTGTCCTGGAACTCCGGAGCTCTGACTTCTGGAGTGCATACTTT
CCCAGCAGTGCTGCAATCTAGCGGACTGTACTCTCTGTCTTCCGTGGTGACTGTGCCT
TCTTCTTCCCTGGGGACTCAAACTTACATCTGCAACGTGAACCACAAGCCCTCCAACA
CCAAGGTGGACAAGAAGGTGGAGCCAAAGAGCTGCGATAAGACCCACACCTGTCCA
CCTTGTCCAGCTCCAGAACTGCTGGGTGGGCCTTCTGTGTTTCTGTTCCCACCTAAGC
CAAAGGATACCCTGATGATCTCTAGGACCCCAGAAGTGACCTGTGTGGTCGTCGATGT
GTCTCATGAAGACCCTGAAGTGAAGTTCAACTGGTACGTGGACGGGGTGGAAGTGCA
TAACGCAAAGACCAAGCCCAGGGAAGAGCAATACAACTCCACCTACAGGGTGGTCTC
CGTCCTGACAGTCCTGCATCAGGATTGGCTGAACGGCAAGGAGTACAAGTGCAAGGT
CTCCAATAAAGCCCTGCCTGCCCCTATCGAGAAAACCATTAGCAAAGCCAAAGGCCA
GCCCAGGGAGCCCCAGGTCTATACACTGCCCCCCAGCAGGGAGGAGATGACAAAAAA
TCAGGTCAGCCTGACATGCCTGGTCAAAGGCTTTTATCCCAGCGACATTGCCGTCGAG
TGGGAGTCCAATGGCCAGCCCGAGAATAATTATAAAACAACACCCCCCGTCCTGGACA
GCGACGGCAGCTTTTTTCTGTATAGCAAACTGACAGTCGATAAAAGCAGGTGGCAGC
AGGGCAATGTCTTTTCCTGCAGCGTCATGCACGAGGCCCTGCACAATCACTATACTCA
GAAAAGCCTGAGCCTGTCCCCCGGGAAATGAGCGGCCGC
```

>459-VHC-1423 bp (SEQ ID NO: 25)
```
gaattcgccgccaccATGAAGCACCTGTGGTTCTTTCTGCTGCTGGTGGCCGCCCCCAGG
TGGGTTCTGAGCCAGGTGCAGCTGCAGGAGAGCGGCCCCGGACTGGTGAAGCCTAG
CGAGACCCTGTCCCTGACCTGCACCGTGTCCGGCGGCTCCATCACCGATTATTTCATG
AACTGGATCAGGCAGCCCCCTGGCAAGGGCCTGGAGTGGATCGGCCGGATCAATCCC
TATAGCGGCGACACCCTGTACAATCAGCGGCTGAAGAGCAGGGTGACCCTGAGCGTG
GATAAGTCCAAGAATCAGGCCAGCCTGAAGCTGTCCTCCGTGACCGCCGCCGACACC
GCTGTGTACTACTGCGGCGGTCGGCCGGTGAGCGGCTTGGATTACTGGGGCCAGGGC
ACCCTGGTGACCGTGTCCAGCgctagcACCAAGGGACCTTCTGTGTTCCCTCTGGCTCCT
TCTTCTAAGTCCACTTCCGGTGGTACAGCAGCTCTGGGTTGTCTGGTGAAGGATTACT
TCCCAGAACCAGTGACTGTGTCCTGGAACTCCGGAGCTCTGACTTCTGGAGTGCATAC
TTTCCCAGCAGTGCTGCAATCTAGCGGACTGTACTCTCTGTCTTCCGTGGTGACTGTG
CCTTCTTCTTCCCTGGGGACTCAAACTTACATCTGCAACGTGAACCACAAGCCCTCCA
ACACCAAGGTGGACAAGAAGGTGGAGCCAAAGAGCTGCGATAAGACCCACACCTGT
CCACCTTGTCCAGCTCCAGAACTGCTGGGTGGGCCTTCTGTGTTTCTGTTCCCACCTA
AGCCAAAGGATACCCTGATGATCTCTAGGACCCCAGAAGTGACCTGTGTGGTCGTCGA
TGTGTCTCATGAAGACCCTGAAGTGAAGTTCAACTGGTACGTGGACGGGGTGGAAGT
GCATAACGCAAAGACCAAGCCCAGGGAAGAGCAATACAACTCCACCTACAGGGTGGT
CTCCGTCCTGACAGTCCTGCATCAGGATTGGCTGAACGGCAAGGAGTACAAGTGCAA
GGTCTCCAATAAAGCCCTGCCTGCCCCTATCGAGAAAACCATTAGCAAAGCCAAAGG
CCAGCCCAGGGAGCCCCAGGTCTATACACTGCCCCCCAGCAGGGAGGAGATGACAAA
AAATCAGGTCAGCCTGACATGCCTGGTCAAAGGCTTTTATCCCAGCGACATTGCCGTC
GAGTGGGAGTCCAATGGCCAGCCCGAGAATAATTATAAAACAACACCCCCCGTCCTG
GACAGCGACGGCAGCTTTTTTCTGTATAGCAAACTGACAGTCGATAAAAGCAGGTGG
CAGCAGGGCAATGTCTTTTCCTGCAGCGTCATGCACGAGGCCCTGCACAATCACTATA
CTCAGAAAAGCCTGAGCCTGTCCCCCGGGAAATGAGCGGCCGC
```

>551-VHB-1423 bp (SEQ ID NO: 26)
```
gaattcgccgccaccATGAAGCACCTGTGGTTCTTCCTGCTGCTGGTGGCTGCTCCTAGGT
GGGTGCTGAGCGAGGTGCAGCTGGTGCAGAGCGGCGCCGAGGTGAAGAAGCCCGGC
GAGAGCCTGAAGATCTCCTGTAAGGCTTCCGGCTACTCCTTCACCGACTACTTTATGA
ATTGGGTGCGGCAGATGCCCGGCAAGGGCCTGGAGTGGATCGGCAGAATCAATCCTT
ACAGCGGCGACACCCTGTACAACCAGCGGCTGCAGGGCCAGGTGACCCTGTCCGCTG
ATAAGAGCATCTCCACCGCCTACCTGCAGCTGTCCTCCCTGAAGGCCTCCGACACCGC
CATGTACTACTGTGCAGGAGCGGCGTGAGCGGCCTGGACTACTGGGGCCAGGGCAC
```

-continued

| DNA sequence |
| --- |

```
CCTGGTGACCGTGAGCAGCgctagcACCAAGGGACCTTCTGTGTTCCCTCTGGCTCCTTC
TTCTAAGTCCACTTCCGGTGGTACAGCAGCTCTGGGTTGTCTGGTGAAGGATTACTTC
CCAGAACCAGTGACTGTGTCCTGGAACTCCGGAGCTCTGACTTCTGGAGTGCATACTT
TCCCAGCAGTGCTGCAATCTAGCGGACTGTACTCTCGTCTTCCGTGGTGACTGTGCC
TTCTTCTTCCCTGGGGACTCAAACTTACATCTGCAACGTGAACCACAAGCCCTCCAAC
ACCAAGGTGGACAAGAAGGTGGAGCCAAAGAGCTGCGATAAGACCCACACCTGTCC
ACCTTGTCCAGCTCCAGAACTGCTGGGTGGGCCTTCTGTGTTTCTGTTCCCACCTAAG
CCAAAGGATACCCTGATGATCTCTAGGACCCCAGAAGTGACCTGTGTGGTCGTCGATG
TGTCTCATGAAGACCCTGAAGTGAAGTTCAACTGGTACGTGGACGGGGTGGAAGTGC
ATAACGCAAAGACCAAGCCCAGGGAAGAGCAATACAACTCCACCTACAGGGTGGTCT
CCGTCCTGACAGTCCTGCATCAGGATTGGCTGAACGGCAAGGAGTACAAGTGCAAGG
TCTCCAATAAAGCCCTGCCTGCCCCTATCGAGAAAACCATTAGCAAAGCCAAAGGCCA
GCCCAGGGAGCCCCAGGTCTATACACTGCCCCCCAGCAGGGAGGAGATGACAAAAAA
TCAGGTCAGCCTGACATGCCTGGTCAAAGGCTTTTATCCCAGCGACATTGCCGTCGAG
TGGGAGTCCAATGGCCAGCCCGAGAATAATTATAAAACAACACCCCCCGTCCTGGACA
GCGACGGCAGCTTTTTTCTGTATAGCAAACTGACAGTCGATAAAAGCAGGTGGCAGC
AGGGCAATGTCTTTTCCTGCAGCGTCATGCACGAGGCCCTGCACAATCACTATACTCA
GAAAAGCCTGAGCCTGTCCCCCGGGAAATGAGCGGCCGC >621-VLA-725 bp
                                              (SEQ ID NO: 27)
gaattcgccgccaccATGGTGCTGCAGACCCAGGTGTTTATCTCCCTGCTGCTGTGGATCA
GCGGCGCCTATGGCGAGATCGTGCTGACCCAGTCCCCTGATTTCCAGAGCGTGACCCC
TAAGGAGAAGGTGACCATCACCTGCAGCGCCAGCAGCTCCGCCAGCTATATGCACTG
GTACCAGCAGAAGCCCGACCAGTCCCCTAAGCGGTGGATCTATGACACCAGCAAGCT
GGCTAGCGGCGTGCCTAGCAGGTTCTCCGGCAGCGGCAGCGGCACCGACTACACCCT
GACCATCAACTCCCTGGAGGCTGAGGACGCCGCCACCTATTACTGCCAGCAGTGGAG
CTCCAACCCCCCTACCTTTGGCGGCGGCACCAAGGTGGAGATCAAGcgtacgGTGGCTG
CACCTTCTGTGTTCATCTTCCCTCCATCTGATGAGCAGCTGAAGTCTGGAACCGCATCT
GTCGTCTGTCTGCTGAACAACTTTTACCCCAGGGAGGCTAAGGTCCAATGGAAGGTG
GACAACGCCCTGCAGTCTGGTAATAGCCAGGAAAGCGTGACCGAACAGGATTCCAAG
GACTCCACCTACTCCCTGTCCTCCACACTGACACTGAGCAAAGCCGACTATGAAAAG
CACAAAGTGTATGCCTGCGAGGTCACTCATCAGGGCCTGTCCAGCCCCGTGACTAAA
AGCTTTAATAGGGGGGAGTGCTGAGCGGCCGC >311-VLA-725 bp
                                              (SEQ ID NO: 28)
gaattcgccgccaccATGGTGCTGCAGACCCAGGTGTTTATCAGCCTGCTGCTGTGGATCA
GCGGCGCCTACGGCGAGATCGTGCTGACCCAGTCCCCCGCCACCCTGTCCCTGTCCCC
AGGAGAGAGGGCTACCCTGAGCTGCTCCGCCAGCTCCAGCGCCTCCTACATCCACTG
GTACCAGCAGAAGCCTGGCCAGGCCCCTCGGAGATGGATGTACGATACCTCCAAGCT
GGCCTCCGGCATCCCCGCCAGATTCAGCGGCAGCGGCAGCGGAACCGATTACACCCT
GACCATCAGCTCCCTGGAGCCTGAGGACGCCGCCGTGTACTACTGCCAGCAGTGGAG
CAGCAACCCTCCTACCTTCGGCGGCGGCACCAAGGTGGAGATCAAGcgtacgGTGGCTG
CACCTTCTGTGTTCATCTTCCCTCCATCTGATGAGCAGCTGAAGTCTGGAACCGCATCT
GTCGTCTGTCTGCTGAACAACTTTTACCCCAGGGAGGCTAAGGTCCAATGGAAGGTG
GACAACGCCCTGCAGTCTGGTAATAGCCAGGAAAGCGTGACCGAACAGGATTCCAAG
GACTCCACCTACTCCCTGTCCTCCACACTGACACTGAGCAAAGCCGACTATGAAAAG
CACAAAGTGTATGCCTGCGAGGTCACTCATCAGGGCCTGTCCAGCCCCGTGACTAAA
AGCTTTAATAGGGGGGAGTGCTGAGCGGCCGC >139-VLA-725 bp
                                              (SEQ ID NO: 29)
gaattcgccgccaccATGGTGCTGCAGACCCAGGTGTTTATCAGCCTGCTGCTGTGGATCA
GCGGCGCTTACGGCGACATCCAGCTGACCCAGTCCCCCCTCCAGCCTGAGCGCTAGCG
TGGGCGACCGGGTGACCATCACCTGCTCCGCCTCCAGCTCCGCCAGCTACATGCACTG
GTACCAGCAGAAGCCCGGCAAGGCCCCCAAGAACTGGATCTATGATACCAGCAAGCT
GGCCAGCGGCGTGCCCAGCAGATTCAGCGGCAGCGGCTCCGGCACCGATTACACCCT
GACCATCAGCTCCCTGCAGCCCGAGGATGCTGCCACCTACTACTGCCAGCAGTGGTCC
TCCAACCCCCCTACCTTTGGCGGCGGCACCAAGGTGGAGATCAAGcgtacgGTGGCTGC
ACCTTCTGTGTTCATCTTCCCTCCATCTGATGAGCAGCTGAAGTCTGGAACCGCATCTG
TCGTCTGTCTGCTGAACAACTTTTACCCCAGGGAGGCTAAGGTCCAATGGAAGGTGG
ACAACGCCCTGCAGTCTGGTAATAGCCAGGAAAGCGTGACCGAACAGGATTCCAAGG
ACTCCACCTACTCCCTGTCCTCCACACTGACACTGAGCAAAGCCGACTATGAAAAGC
ACAAAGTGTATGCCTGCGAGGTCACTCATCAGGGCCTGTCCAGCCCCGTGACTAAAA
GCTTTAATAGGGGGGAGTGCTGAGCGGCCGC >12-VHA
                                              (SEQ ID NO: 30)
MKHLWFFLLLVAAPRWVLSQVQLVQSGAEVKKPGASVKVSCKASGYSFTDYFMN
WVRQAPGQGLEWIGRINPYSGDTLYNQRLKGRATLTVDKSISTAYMELSRLRSDDTAVYY
CGRSGVSGLDYWGQGTLVTVSSASTKGPSVFPLAPSSKSTSGGTAALGCLVKDYFPEPVT
VSWNSGALTSGVHTFPAVLQSSGLYSLSSVVTVPSSSLGTQTYICNVNHKPSNTKVDKKV
EPKSCDKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIEK
```

-continued

---
DNA sequence
---

TISKAKGQPREPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLSPGK;
SIP:[1:19], Human IgG1 constant region: [137:466]

>12-VHB (SEQ ID NO: 31)

MKHLWFFLLLVAAPRWVLSQVQLVQSGAEVKKPGASVKVSCKASGYSFTDYFMN
WVRQAPGQGLEWIGRINPYSGDTLYNQKLQGRVTMTVDKSISTAYMELSRLRSDDTAVY
YCGRSGVSGLDYWGQGTLVTVSSASTKGPSVFPLAPSSKSTSGGTAALGCLVKDYFPEPV
TVSWNSGALTSGVHTFPAVLQSSGLYSLSSVVTVPSSSLGTQTYICNVNHKPSNTKVDKK
VEPKSCDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIE
KTISKAKGQPREPQVYTLPPSREEMTKNQVSLTCLVKGFYPSDIAVEWESNGQPENNYKT
TPPVLDSDGSFFLYSKLTVDKSRWQQGNVFSCSVMHEALHNHYTQKSLSLSPGK;
SIP:[1:19], Human IgG1 constant region: [137:466]

>459-VHA (SEQ ID NO: 32)

MKHLWFFLLLVAAPRWVLSQVQLQESGPGLVKPSETLSLTCTASGYSFTDYFMNWV
RQPPGKGLEWIGRINPYSGDTLYNQRLKGRVTLSVDKSKNQASLKLSSVTAADTAVYYC
GRSGVSGLDYWGQGTLVTVSSASTKGPSVFPLAPSSKSTSGGTAALGCLVKDYFPEPVTV
SWNSGALTSGVHTFPAVLQSSGLYSLSSVVTVPSSSLGTQTYICNVNHKPSNTKVDKKVE
PKSCDKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESNGQPENNYKTTPP
VLDSDGSFFLYSKLTVDKSRWQQGNVFSCSVMHEALHNHYTQKSLSLSPGK;
SIP:[1:19], Human IgG1 constant region: [137:466]

>459-VHB (SEQ ID NO: 33)

MKHLWFFLLLVAAPRWVLSQVQLQESGPGLVKPSETLSLTCTASGYSFTDYFMNWIR
QPPGKGLEWIGRINPYSGDTLYNQRLKSRVTLSVDKSKNQASLKLSSVTAADTAVYYCGR
SGVSGLDYWGQGTLVTVSSASTKGPSVFPLAPSSKSTSGGTAALGCLVKDYFPEPVTVSW
NSGALTSGVHTFPAVLQSSGLYSLSSVVTVPSSSLGTQTYICNVNHKPSNTKVDKKVEPKS
CDKTHTCPPCPAPELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALPAPIEKTISK
AKGQPREPQVYTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPGK;
SIP:[1:19], Human IgG1 constant region: [137:466]

>459-VHC (SEQ ID NO: 34)

MKHLWFFLLLVAAPRWVLSQVQLQESGPGLVKPSETLSLTCTVSGGSITDYFMNWIR
QPPGKGLEWIGRINPYSGDTLYNQRLKSRVTLSVDKSKNQASLKLSSVTAADTAVYYCGR
SGVSGLDYWGQGTLVTVSSASTKGPSVFPLAPSSKSTSGGTAALGCLVKDYFPEPVTVSW
NSGALTSGVHTFPAVLQSSGLYSLSSVVTVPSSSLGTQTYICNVNHKPSNTKVDKKVEPKS
CDKTHTCPPCPAPELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALPAPIEKTISK
AKGQPREPQVYTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPGK;
SIP:[1:19], Human IgG1 constant region: [137:466]

>551-VHB (SEQ ID NO: 35)

MKHLWFFLLLVAAPRWVLSEVQLVQSGAEVKKPGESLKISCKASGYSFTDYFMNW
VRQMPGKGLEWIGRINPYSGDTLYNQRLQGQVTLSADKSISTAYLQLSSLKASDTAMYY
CGRSGVSGLDYWGQGTLVTVSSASTKGPSVFPLAPSSKSTSGGTAALGCLVKDYFPEPVT
VSWNSGALTSGVHTFPAVLQSSGLYSLSSVVTVPSSSLGTQTYICNVNHKPSNTKVDKKV
EPKSCDKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIEK
TISKAKGQPREPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLSPGK;
SIP:[1:19], Human IgG1 constant region: [137:466]

>621-VLA (SEQ ID NO: 36)

MVLQTQVFISLLLWISGAYGEIVLTQSPDFQSVTPKEKVTITCSASSSASYMHWYQQ
KPDQSPKRWIYDTSKLASGVPSRFSGSGSGTDYTLTINSLEAEDAATYYCQQWSSNPPTFG
GGTKVEIKRTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC;
SIP:[1:20], Human kappa constant region: [127:233]

>311-VLA (SEQ ID NO: 37)

MVLQTQVFISLLLWISGAYGEIVLTQSPATLSLSPGERATLSCSASSSASYIHWYQQKP
GQAPRRWMYDTSKLASGIPARFSGSGSGTDYTLTISSLEPEDAAVYYCQQWSSNPPTFGG

-continued

| DNA sequence |
| --- |

GTKVEIKRTVAAPSVFIFPPSDEQLKSGTASVVCLLNNFYPREAKVQWKVDNALQSGNSQ
ESVTEQDSKDSTYSLSSTLTLSKADYEKHKVYACEVTHQGLSSPVTKSFNRGEC;
SIP:[1:20], Human kappa constant region: [127:233]

>139-VLA (SEQ ID NO: 38)
MVLQTQVFISLLLWISGAYGDIQLTQSPSSLSASVGDRVTITCSASSSASYMHWYQQKPGK
APKNWIYDTSKLASGVPSRFSGSGSGTDYTLTISSLQPEDAATYYCQQWSSNPPTFGGGT
KVEIKRTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC;
SIP:[1:20], Human kappa constant region: [127:233]

(3) Transient Transfection

Endotoxin-free plasmid DNA was extracted. The CHO-K1 cells were co-transfected with the constructed vectors and then cultured. When the survival rate reduced below 50%, the culture supernatant was collected from a part of cells, antibodies were purified by using protein G and subjected to SDS-PAGE on gel. The activity of antibody was detected by ELISA using antigen protein.

Transfection Method

<1> One day prior to transfection, $27 \times 10^6$ cells were seeded in the complete culture medium (without antibiotics and anti-aggregation reagents) and reached logarithmic growth phase at the day of transfection.

<2> Preparation of a transfection mixture a. DNA was diluted in a part of complete medium and mixed gently.

b. PEI transfection reagent was diluted in another part of complete medium, mixed gently, and incubated at room temperature for 5 minutes.

c. The diluted PEI was added to the diluted DNA in a total volume of 3 ml of the mixture, mixed gently, and incubated at room temperature for 20-30 minutes.

<3> Transfection was carried out as follows. 3 ml of the transfection mixture was added to 27 ml of cell suspension, mixed gently, and incubated at 37° C., 5% $CO_2$, 130 rpm until the cell survival rate reduces below 50%. Samples were collected.

Table 1 shows the details of the transfection.

TABLE 1

| | Combination of transfection (Name of Antibody) | HC | LC |
| --- | --- | --- | --- |
| 1 | 45-2-G3-1-G7-B7-12-VHA/621-VLA | 12-VHA | 621-VLA |
| 2 | 45-2-G3-1-G7-B7-12-VHA/311-VLA | | 311-VLA |

TABLE 1-continued

| | Combination of transfection (Name of Antibody) | HC | LC |
| --- | --- | --- | --- |
| 3 | 45-2-G3-1-G7-B7-12-VHA/139-VLA | | 139-VLA |
| 4 | 45-2-G3-1-G7-B7-12-VHB/621-VLA | 12-VHB | 621-VLA |
| 5 | 45-2-G3-1-G7-B7-12-VHB/311-VLA | | 311-VLA |
| 6 | 45-2-G3-1-G7-B7-12-VHB/139-VLA | | 139-VLA |
| 7 | 45-2-G3-1-G7-B7-459-VHA/621-VLA | 459-VHA | 621-VLA |
| 8 | 45-2-G3-1-G7-B7-459-VHA/311-VLA | | 311-VLA |
| 9 | 45-2-G3-1-G7-B7-459-VHA/139-VLA | | 139-VLA |
| 10 | 45-2-G3-1-G7-B7-459-VHB/621-VLA | 459-VHB | 621-VLA |
| 11 | 45-2-G3-1-G7-B7-459-VHB/311-VLA | | 311-VLA |
| 12 | 45-2-G3-1-G7-B7-459-VHB/139-VLA | | 139-VLA |
| 13 | 45-2-G3-1-G7-B7-459-VHC/621-VLA | 459-VHC | 621-VLA |
| 14 | 45-2-G3-1-G7-B7-459-VHC/311-VLA | | 311-VLA |
| 15 | 45-2-G3-1-G7-B7-459-VHC/139-VLA | | 139-VLA |
| 16 | 45-2-G3-1-G7-B7-551-VHB/621-VLA | 551-VHB | 621-VLA |
| 17 | 45-2-G3-1-G7-B7-551-VHB/311-VLA | | 311-VLA |
| 18 | 45-2-G3-1-G7-B7-551-VHB/139-VLA | | 139-VLA |

(4) Purification

Figure 4:
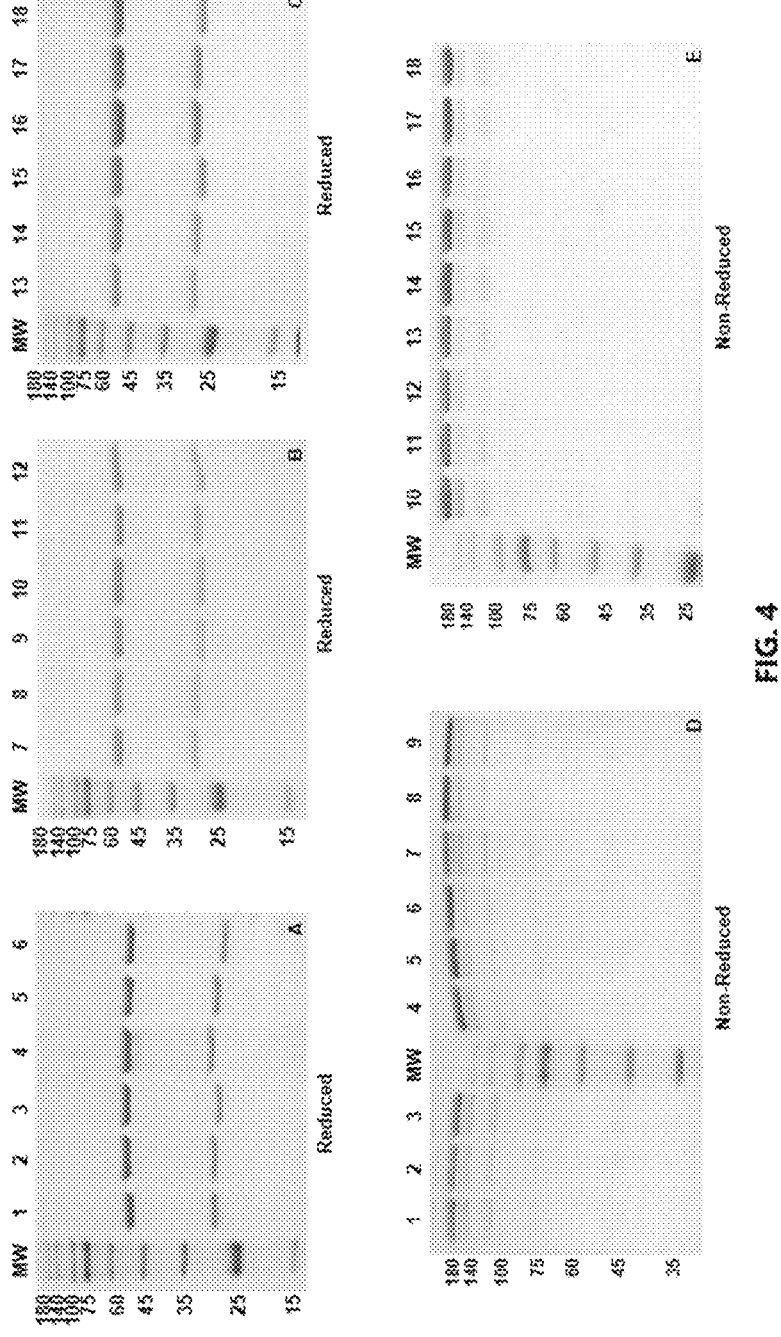
FIG. 4 shows the results of the purification.

The supernatants were collected by centrifugation and loaded onto 18 Protein A purification columns (1 ml) respectively, and the packing was equilibrated with PBS with a pH of 7.5. The supernatant was mixed well with Protein A resin and incubated overnight and then purified. The PBS buffer with a pH of 7.0 was used for washing, 20 mM citric acid buffer with a pH of 2.7 was used for elution, and 1 M Tris HCl (neutralization buffer) was used for neutralization pH from 9.0 to 6.0. After purification, 20 μl of each of the IN, FT, washed samples and eluted samples were subjected to SDS-PAGE. The samples were collected based on the SDS-PAGE results and dialyzed overnight, and then the samples were pooled and subjected to the buffer exchange and concentration. The final results are shown in FIG. 4 and Table 2.

TABLE 2

| Number | Antibody | Concentration | Quantity | Number | Yield |
| --- | --- | --- | --- | --- | --- |
| 1 | 12-VHA/621-VLA | 1.05 mg/ml | 0.50 mg/vial | 1 vial | 0.50 mg |
| 2 | 12-VHA/311-VLA | 1.16 mg/ml | 0.50 mg/vial | 1 vial | 0.50 mg |
| 3 | 12-VHA/139-VLA | 1.31 mg/ml | 0.50 mg/vial | 1 vial | 0.50 mg |
| 4 | 12-VHB/621-VLA | 1.01 mg/ml | 0.50 mg/vial | 1 vial | 0.50 mg |
| 5 | 12-VHB/311-VLA | 1.00 mg/ml | 0.50 mg/vial | 1 vial | 0.50 mg |
| 6 | 12-VHB/139-VLA | 1.13 mg/ml | 0.50 mg/vial | 1 vial | 0.50 mg |
| 7 | 459-VHA/621-VLA | 0.96 mg/ml | 0.50 mg/vial | 1 vial | 0.50 mg |
| 8 | 459-VHA/311-VLA | 1.02 mg/ml | 0.50 mg/vial | 1 vial | 0.50 mg |
| 9 | 459-VHA/139-VLA | 1.07 mg/ml | 0.50 mg/vial | 1 vial | 0.50 mg |
| 10 | 459-VHB/621-VLA | 0.80 mg/ml | 0.50 mg/vial | 1 vial | 0.50 mg |
| 11 | 459-VHB/311-VLA | 1.13 mg/ml | 0.50 mg/vial | 1 vial | 0.50 mg |
| 12 | 459-VHB/139-VLA | 1.25 mg/ml | 0.50 mg/vial | 1 vial | 0.50 mg |
| 13 | 459-VHC/621-VLA | 0.69 mg/ml | 0.50 mg/vial | 1 vial | 0.50 mg |
| 14 | 459-VHC/311-VLA | 1.00 mg/ml | 0.50 mg/vial | 1 vial | 0.50 mg |
| 15 | 459-VHC/139-VLA | 1.16 mg/ml | 0.50 mg/vial | 1 vial | 0.50 mg |

TABLE 2-continued

| Number | Antibody | Concentration | Quantity | Number | Yield |
|---|---|---|---|---|---|
| 16 | 551-VHB/621-VLA | 1.78 mg/ml | 0.50 mg/vial | 1 vial | 0.50 mg |
| 17 | 551-VHB/311-VLA | 1.71 mg/ml | 0.50 mg/vial | 1 vial | 0.50 mg |
| 18 | 551-VHB/139-VLA | 1.80 mg/ml | 0.50 mg/vial | 1 vial | 0.50 mg |

Figure 5:
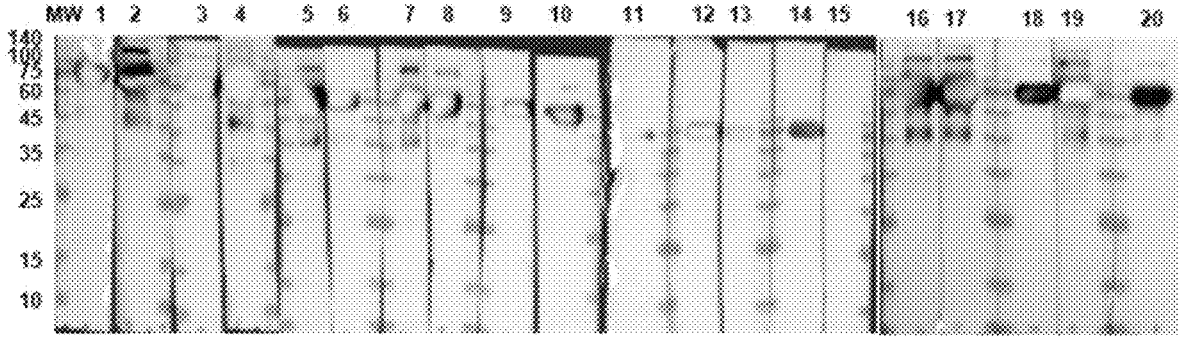
FIG. 5 shows ELISA results for 18 humanized antibodies.

The specific binding was verified by Western Blot. The results are shown in Table 3 and FIG. 5, wherein 1-18 represent 18 humanized monoclonal antibodies, the 19009414P 11 (human IgG1) represents a chimeric periostin antibody and the 45-2-G3-1-G7-B7 represents a murine periostin monoclonal antibody.

TABLE 3

| Periostin-Mouse | Primary antibody | Secondary antibody | |
|---|---|---|---|
| 1 | 12-VHA/621-VLA | Goat Anti Human | Positive |
| 2 | 12-VHA/311-VLA | | Positive |
| 3 | 12-VHA/139-VLA | | Positive |
| 4 | 12-VHB/621-VLA | | positive |
| 5 | 12-VHB/311-VLA | | Positive |
| 6 | 12-VHB/139-VLA | | Positive |
| 7 | 459-VHA/621-VLA | | Positive |

TABLE 3-continued

| Periostin-Mouse | Primary antibody | Secondary antibody | |
|---|---|---|---|
| 8 | 459-VHA/311-VLA | | Positive |
| 9 | 459-VHA/139-VLA | | Positive |
| 10 | 459-VHB/621-VLA | | Positive |
| 11 | 459-VHB/311-VLA | | Positive |
| 12 | 459-VHB/139-VLA | | Positive |
| 13 | 459-VHC/621-VLA | | Positive |
| 14 | 459-VHC/311-VLA | | Positive |
| 15 | 459-VHC/139-VLA | | Positive |
| 16 | 551-VHB/621-VLA | | Positive |
| 17 | 551-VHB/311-VLA | | Positive |
| 18 | 551-VHB/139-VLA | | Positive |
| 19 | 19009414P 11 (human IgG1) | | Positive |
| 20 | 45-2-G3-1-G7-B7 | Goat Anti Mouse | Positive |

Arrangement of humanized antibodies on a plate for ELISA is shown in Table 4.

TABLE 4

| 1 | 2 | 3 | 4 | 5 | 6 | 7 | 8 |
|---|---|---|---|---|---|---|---|
| 12-VHA/621-VLA | 12-VHA/621-VLA | 12-VHA/621-VLA | 459-VHA/139-VLA | 459-VHA/139-VLA | 459-VHA/139-VLA | 551-VHB/311-VLA | 19009414P11 |
| 12-VHA/311-VLA | 12-VHA/311-VLA | 12-VHA/311-VLA | 459-VHB/621-VLA | 459-VHB/621-VLA | 459-VHB/621-VLA | 551-VHB/311-VLA | 19009414P11 |
| 12-VHA/139-VLA | 12-VHA/139-VLA | 12-VHA/139-VLA | 459-VHB/311-VLA | 459-VHB/311-VLA | 459-VHB/311-VLA | 551-VHB/311-VLA | 19009414P11 |
| 12-VHB/621-VLA | 12-VHB/621-VLA | 12-VHB/621-VLA | 459-VHB/139-VLA | 459-VHB/139-VLA | 459-VHB/139-VLA | 551-VHB/139-VLA | 45-2-G3-1-G7-B7 |
| 12-VHB/311-VLA | 12-VHB/311-VLA | 12-VHB/311-VLA | 459-VHC/621-VLA | 459-VHC/621-VLA | 459-VHC/621-VLA | 551-VHB/139-VLA | 45-2-G3-1-G7-B7 |
| 12-VHB/139-VLA | 12-VHB/139-VLA | 12-VHB/139-VLA | 459-VHC/311-VLA | 459-VHC/311-VLA | 459-VHC/311-VLA | 551-VHB/139-VLA | 45-2-G3-1-G7-B7 |
| 459-VHA/621-VLA | 459-VHA/621-VLA | 459-VHA/621-VLA | 459-VHC/139-VLA | 459-VHC/139-VLA | 459-VHC/139-VLA | Negative control | Negative control |
| 459-VHA/311-VLA | 459-VHA/311-VLA | 459-VHA/311-VLA | 551-VHB/621-VLA | 551-VHB/621-VLA | 551-VHB/621-VLA | Negative control | Negative control |

Results of ELISA assay are shown in Table 5.

TABLE 5

| 1 | 2 | 3 | 4 | 5 | 6 | 7 | 8 |
|---|---|---|---|---|---|---|---|
| 2.2676 | 2.1962 | 2.1325 | 1.0578 | 1.0122 | 1.0485 | 2.0413 | 1.7380 |
| 2.3149 | 2.2910 | 2.1548 | 1.9094 | 1.9964 | 1.9358 | 1.9902 | 1.6759 |
| 1.8726 | 1.9203 | 1.8613 | 2.0560 | 1.8604 | 1.8602 | 1.9714 | 1.6779 |
| 2.1021 | 1.9955 | 1.9839 | 0.4797 | 0.4511 | 0.4934 | 1.7166 | 0.7665 |
| 2.1828 | 2.1139 | 2.0769 | 1.1582 | 1.0934 | 1.0282 | 1.7625 | 0.7699 |
| 2.0264 | 2.1278 | 2.1131 | 0.6429 | 0.5133 | 0.5998 | 1.7652 | 0.6939 |
| 1.8504 | 1.9261 | 1.9378 | 0.0641 | 0.0639 | 0.0626 | 0.0619 | 0.0555 |
| 2.0901 | 2.2168 | 2.1762 | 2.0171 | 2.1129 | 2.0738 | 0.0554 | 0.0567 |

Figure 6:
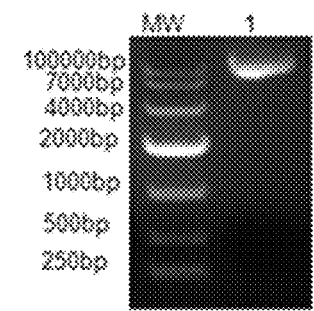
FIG. 6 shows the detection of expression vector by electrophoresis.

3. Construction of the Stable Transgenic Cell Line and Expression of the Humanized Antibody (1) Construction of Vector From the results of transient transfection, it can be seen that the number 18th antibody 551-VHB/139-VLA has the highest expression and the binding ability meets the requirements. Therefore, considering the expression and the binding ability of antibodies, 551-VHB and 139-VLA were selected to use as the heavy and light chain of the humanized periostin antibody. The DNAs encoding 551-VHB and 139-VLA were subcloned into the pATX-GS2 expression vector respectively, and then co-transfected into CHO cells to express the antibody protein. The results of agarose gel electrophoresis are shown in FIG. 6.

(2) Expression of the Humanized Periostin Antibody

The target fragment was subcloned into the expression vector pATX-GS2 after double enzyme digestion (EcoR I/Not I) and ligation, and then stably transfected into CHO cells. Stable cell lines were obtained through MSX pressure screening and limited dilution by ELISA. The stable cell line was incubated in a shaker incubator with 5% $CO_2$ at 37° C., for 7 days, and then the supernatant was collected, and the humanized antibodies in the supernatant were purified by affinity chromatography column packed with agarose gel-Protein A.

<1> Linearization of Plasmid

Figure 7:
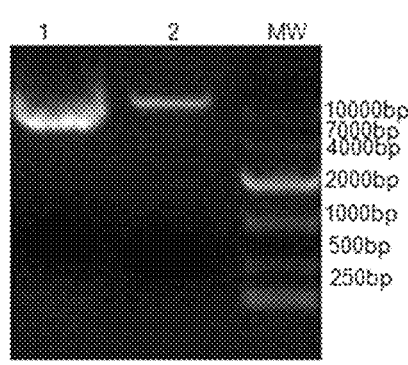
FIG. 7 shows the detection results of linearized expression vector by electrophoresis.

10 μl of extracted plasmid PATX-GS2-139-VLA-551-VHB (backup) was reserved in advance to verify the success of linearization. Enzymes and buffer were added to the plasmid for linearization sequentially and mixed well. The EP tube was inserted into the water-bath float, and putted into the water-bath at 37° C. to perform the enzyme digestion for about 1-2 hours. After enzymatic digestion, the plasmid was recovered as follows. 0.75 times isopropanol (based on the volume of the digestion system) was added to the digestion system and mixed well, and centrifuged at 4° C. for 30 minutes. The supernatant was discarded; 1 ml of 70% ethanol was added and centrifuged at 4° C. for 5 minutes. The concentration was measured by agarose gel electrophoresis (FIG. 7).

Enzyme digestion system is shown in Table 6.

TABLE 6

| Reagents | Volume (μl) |
| --- | --- |
| Buffer | 10 |
| Plasmid | all |
| Enzyme | 6-10 |

<2> Transfection

CHO-K1 cells were transfected chemically with PVUI-linearized plasmid pATX-GS2-139-VLA-551-VHB by using FectoCHO™ Expression System Transfection Kit to obtain a stable transgenic cell pool expressing recombinant antibody.

<3> Screening by Pressure

At 48 hours post-transfection, the transfected host cells were selected by using GS selection system (glutamine synthetase Gene Expression System). The cells were treated under selective pressure using 30 μM MSX. The natural resistance of the CHO-K1 cells to MSX was determined separately in 6-well plates by standard batch culture. The minimum killing concentration of MSX against non-transfected CHO-K1 cells was determined to be 20 μM. The transfected cells were treated with 30 μM MSX. The medium was replaced with fresh medium every 3-4 days until a stable cell line with resistance was generated. 3 stable cell pools were generated after 2 to 3 weeks under MSX selection.

Figure 8:
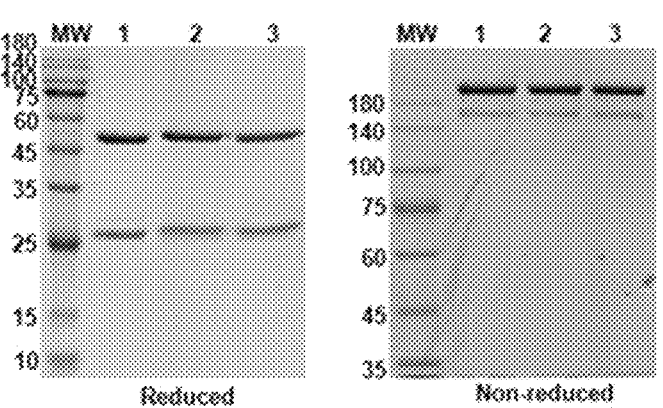
FIG. 8 shows the results of protein expression and purification after screening.

Cells were cultured in 30 ml selective medium in a 125 ml shake flask under standard conditions (37° C., 5% $CO_2$, 130 rpm). For expression assay, when the cells were in good condition in the shake flask, a 30 ml fed-batch culture was carried out. Media supplement was added on D3, D5, D7 and D9 respectively and the glucose was monitored throughout. The cells were cultured consistently for consecutive 3 passages until the cell viability reduced below 50%, and the supernatants of the culture were collected, purified and analyzed. The purification results are shown in FIG. 8, where "reduced" represents the results of reduced SDS-PAGE and "non-reduced" represents the results of non-reduced SDS-PAGE.

Sample information is shown in Table 7.

TABLE 7

| Antibody | Concentration | Specification | Quantity | Yield |
| --- | --- | --- | --- | --- |
| 18-stable 1 | 0.86 mg/ml | 1.75 ml/vial | 4 vials | 6.02 mg/30 ml |
| 18-stable 2 | 0.94 mg/ml | 1.80 ml/vial | 4 vials | 6.76 mg/30 ml |
| 18-stable 3 | 1.62 mg/ml | 1.80 ml/vial | 4 vials | 11.66 mg/30 ml |

(4) Isolation of Monoclonal Antibodies by Limiting Dilution

The stable pool 3 (18-stable 3) polyclonal cells were selected and plated for limiting dilution under selective pressure. The cell suspension of the obtained stable transgenic pool was diluted to a very low density, allowing an average of 1 cell per well. A total of 7 monoclonal cell lines, 5-G4, 5-E6, 5-G6, 5-D7, 5-G9, 2-H3 and 2-C7, with high expression were selected after ELISA for subsequent expansion culture. The antibody concentrations is sequentially 1, 0.33, 0.11, 0.037, 0.012, 0.004, 0.0014 μg/ml (1:3-fold dilution gradient), plus a blank control for a total of 8 gradients. The mono-clones were observed under the microscope and the positive mono-clones were detected by ELSIA. The results of ELISA are shown Table 8.

TABLE 8

| | | 5-E6 | | 2-C7 | | 5-G4 | | 5-G6 | | 5-G9 | |
| --- | --- | --- | --- | --- | --- | --- | --- | --- | --- | --- | --- |
| | A | 3.396 | 3.3316 | 3.4232 | 3.5079 | 3.3039 | 3.4063 | 3.3018 | 3.4721 | 3.2732 | 3.2581 |
| | B | 2.6476 | 2.546 | 2.9524 | 2.9827 | 2.5342 | 2.6667 | 2.6281 | 2.8172 | 2.5232 | 2.4339 |
| | C | 2.0211 | 2.0248 | 2.4196 | 2.4409 | 1.9811 | 2.1821 | 1.7536 | 1.8631 | 1.7679 | 1.7009 |
| | D | 1.2649 | 1.2504 | 1.6714 | 1.703 | 1.2489 | 1.3418 | 0.8885 | 0.9864 | 0.9552 | 0.9643 |
| | E | 0.5966 | 0.6148 | 0.8319 | 0.9243 | 0.6348 | 0.6621 | 0.3714 | 0.4403 | 0.3928 | 0.4166 |
| | F | 0.2681 | 0.2774 | 0.3728 | 0.419 | 0.2898 | 0.2986 | 0.1667 | 0.2001 | 0.1851 | 0.1931 |
| | G | 0.1589 | 0.1475 | 0.1692 | 0.178 | 0.1513 | 0.166 | 0.1023 | 0.1171 | 0.1076 | 0.1142 |
| | H | 0.0725 | 0.07 | 0.0714 | 0.0737 | 0.072 | 0.0747 | 0.0714 | 0.0768 | 0.0806 | 0.0734 |

TABLE 8-continued

| | | 2-H3 | | 5-D7 | | Ab18 | |
|---|---|---|---|---|---|---|---|
| | A | 3.5402 | 3.5486 | 3.2889 | 3.3281 | 2.288 | 2.3394 |
| | B | 3.0076 | 3.0135 | 2.6347 | 2.66 | 1.1352 | 1.2038 |
| | C | 2.4923 | 2.578 | 1.8413 | 1.84 | 0.5058 | 0.5265 |
| | D | 1.7786 | 1.7678 | 1.0517 | 1.0929 | 0.2432 | 0.2399 |
| | E | 0.9525 | 0.9749 | 0.4927 | 0.4684 | 0.1247 | 0.1345 |
| | F | 0.44 | 0.4441 | 0.2196 | 0.2178 | 0.0837 | 0.0885 |
| | G | 0.2294 | 0.2096 | 0.1256 | 0.1277 | 0.0746 | 0.075 |
| | H | 0.0752 | 0.0748 | 0.0765 | 0.0771 | 0.0706 | 0.072 |

Figure 9:
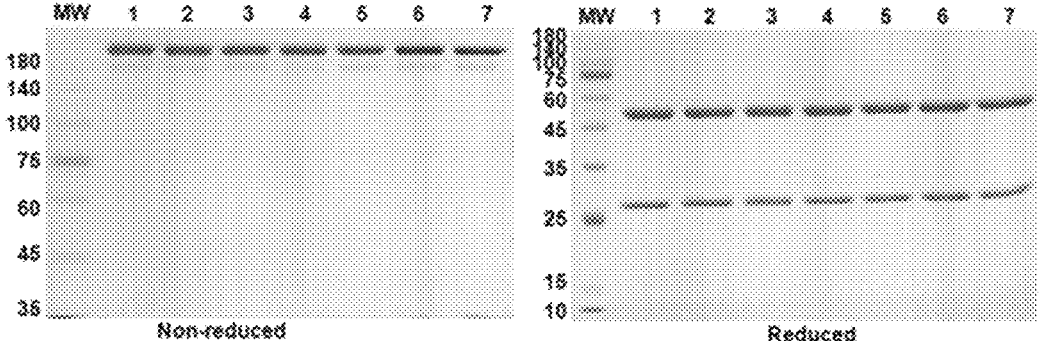
FIG. 9 shows the results of protein expression and purification in cells obtained after screening.

Cells of clone 5-G4, 2-C7, 5-E6, 5-G9, 2-H3, 5-D7 and 5-G6 were cultured in 30 ml of selective medium in a 125 ml shake flask under standard conditions (37° C., 5% $CO_2$, 130 rpm/minute) for 3 passages. For expression assay, when the cells were in good condition in the shake flask, a 30 ml fed-batch culture was carried out. Media supplement was added on D3, D5, D7 and D9 respectively and the glucose was monitored throughout until the cell viability reduced below 50%. The supernatants of the culture were collected and purified. The purification results are shown in FIG. 9.

Sample information is shown in Table 9.

TABLE 9

| Anti-body | Concen-tration | Volume | Quantity | Yield | Yield |
|---|---|---|---|---|---|
| 5-E6 | 4.49 mg/ml | 1.63 ml/vial | 7 vials | 51.23 mg/30 ml | 1.70 g/L |
| 5-G4 | 7.13 mg/ml | 1.64 ml/vial | 7 vials | 81.86 mg/30 ml | 2.72 g/L |
| 2-H3 | 3.91 mg/ml | 1.67 ml/vial | 7 vials | 45.71 mg/30 ml | 1.52 g/L |
| 5-D7 | 4.63 mg/ml | 1.55 ml/vial | 6 vials | 43.06 mg/30 ml | 1.44 g/L |
| 2-C7 | 3.64 mg/ml | 1.63 ml/vial | 7 vials | 41.53 mg/30 ml | 1.38 g/L |
| 5-G6 | 5.07 mg/ml | 1.65 ml/vial | 7 vials | 58.56 mg/30 ml | 1.95 g/L |
| 5-G9 | 6.14 mg/ml | 1.61 ml/vial | 7 vials | 69.20 mg/30 ml | 2.31 g/L |

(5) Identification of Humanized Anti-Periostin Antibodies

Based on the expression and ELISA results, three stable transfected cell lines (5-G4, 5-G6 and 5-G9) were selected and used for WB detection to verify the binding specificity.

Experimental conditions: 1 µg of antigen, primary antibody (dilution at 1:1000), 1 hour of incubation, secondary antibody (dilution at 1:10000), 45 minutes of incubation. The results are shown in FIG. 10.

Figure 10:
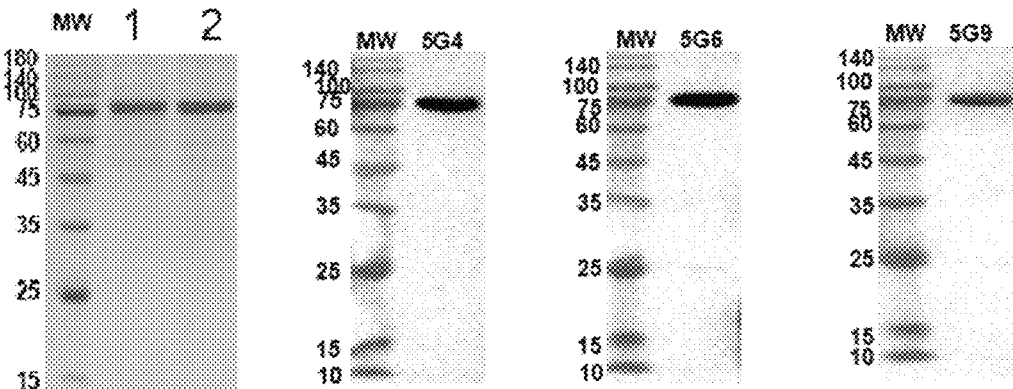
FIG. 10 shows the identification results for humanized anti-periostin antibodies 5-G4, 5-G6 and 5-G9.

As shown in FIG. 10, three stable transfected lines (5-G4, 5-G6 and 5-G9) specifically bound to periostin protein.

4. Anti-Fibrotic Effect of the Humanized Anti-Periostin Antibody 4.1 Method

The antibody from stable transgenic cell line 5-G6 was used for transwell migration assay and for studying the number of migrated cells of fibroblasts, in vivo and in vitro. The fibroblast migration in mice was analyzed by immunohistochemical technology, and the histopathological changes in mice were detected by HE and Masson staining, the area ratio of fibrotic tissue was also studies. The mRNA expression of type I collagen (Col1a1 and Col1a2) and type III collagen (Col3a1) in the mouse model of fibrosis was detected by the real-time fluorescence quantitative polymerase chain reaction (PCR). The experiments included the conditioned medium containing periostin+control IgG as the IgG control group, and the conditioned medium containing periostin+humanized periostin antibody recorded as the Postn nAb group.

The area ratio of fibrotic tissue, the number of positive infiltrating fibroblasts, the ratio of fibroblasts and the median number of migrated fibroblasts were analyzed using Wilcoxon rank-sum test.

Finally, the experimental data was processed using SPSS Statistical Software, and variance between groups was analyzed by ANOVA, with significance defined as $p<0.05$ in all statistical analysis.

4.2 Results 4.2.1 In the transwell migration assay, the number of migrated fibroblasts in the blank control group was much larger than that in the Postn nAb group, which means that the Postn nAb is able to effectively inhibit the migration of fibroblasts and also confirmed the effectiveness of Postn nAb in vitro.

4.2.2 At 14 dpi, the immunohistological analysis results showed that Postn nAb reduced the number of infiltrating fibroblasts compared to the blank control.

4.2.3 The area ratio of fibrotic tissue at 28 dpi showed a significant reduction in fibrotic tissue in mice of Postn nAb group compared to the blank control.

4.2.4 The mRNA expression of collagen type I and collagen type III in mice of Postn nAb group was significantly reduced compared to the blank control group ($P<0.05$).

Conclusion

A humanized anti-periostin monoclonal antibody is successfully produced by the present invention, and the humanized anti-periostin monoclonal antibody was able to specifically bind to periostin protein in vivo, thereby effectively inhibiting the fibrosis in vivo, so the humanized anti-periostin monoclonal antibody has the potential to be a novel medicament for the treatment of retinal fibrosis.

Figure 11:
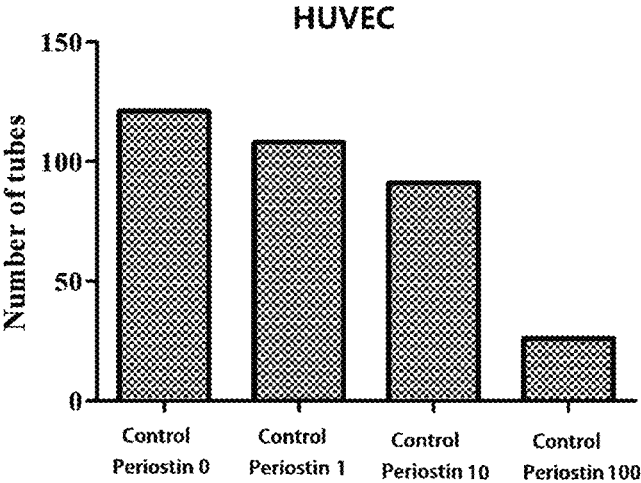
FIG. 11 shows the results of tube formation inhibition assay, wherein the Periostin antibody is a humanized monoclonal antibody and the control Periostin is a murine monoclonal antibody.
Figure 11:
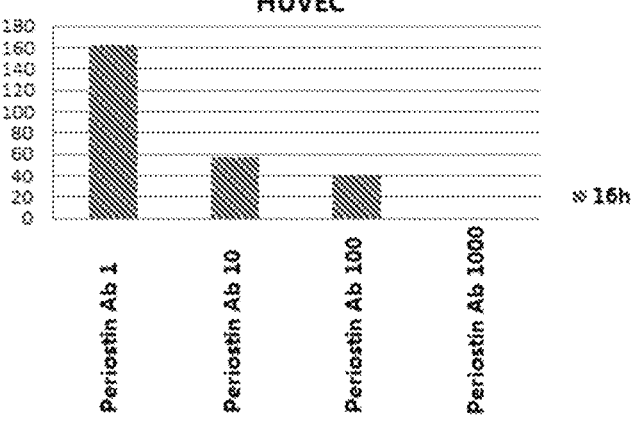

5. Activity of Humanized Periostin Monoclonal Antibody In Vitro 5.1 Tube Formation Inhibition Assay HUVEC cells were plated at 50,000 cells/well (24 h) in a 12-well plate, cultured at 5% $CO_2$, 37° C. overnight in vitro, and then treated with the humanized periostin monoclonal antibody for 16 hours. The tube formation assay was performed. The cells were observed and photographed at desired time points. The statistical analysis results of the experimental data were shown in Table 10 and FIG. 11.

TABLE 10

| HUVEC | Number of tubes | HUVEC | Number of tubes |
|---|---|---|---|
| Group (µg/mL) | 16 h | Group (µg/mL) | 16 h |
| Control periostin 0 | 121 | periostin antibody 1 | 162 |
| Control periostin 1 | 108 | periostin antibody 10 | 57 |
| Control periostin 10 | 91 | periostin antibody 100 | 41 |
| Control periostin 100 | 26 | periostin antibody 1000 | 2 |

As can be seen from the above table, the number of tubes was reduced with increasing antibody concentration, and the tube formation inhibition rate by the humanized monoclonal antibody was greater than that by murine monoclonal antibody at the same concentration, which confirms that the above humanized periostin monoclonal antibody is bale to inhibit the tube formation of human vascular endothelial cells.

5.2 Cultivation of RPE Cells In Vitro and Grouping for Cell Migration Assay, Cell Invasion Assay and Cell Scratch Assay a. Blank control group (Control): without recombinant periostin protein or antibody b. Periostin group: with only periostin protein c. Control IgG group: with periostin+control IgG d. Periostin antibody group: with periostin+Postn nAb Postn nAb: the humanized anti-periostin antibody produced by the present invention 5.2.1 Cell Migration Assay Transwell Assay (1) Cells were centrifuged and then the culture medium was discarded. The cells were washed 1-2 times with PBS, resuspended in serum-free DMEM medium, and the cell density was adjusted to $1 \times 10^5$ cells/ml.

(2) 200 µl of cell suspension was added to the transwell chamber, 600 µl/well of medium containing 10% FBS was added the lower chamber of a 24-well plate and incubated at 37° C. for 16-24 hours.

(3) The 24-well plate was removed, the medium in the transwell chamber was discarded, and the transwell chamber was washed twice with PBS.

(4) Cells were fixed with 4% PFA for 10 minutes and washed twice with PBS.

(5) The cells were subjected to Crystalline Violet staining for 10 minutes, washed twice with PBS.

Figure 12:
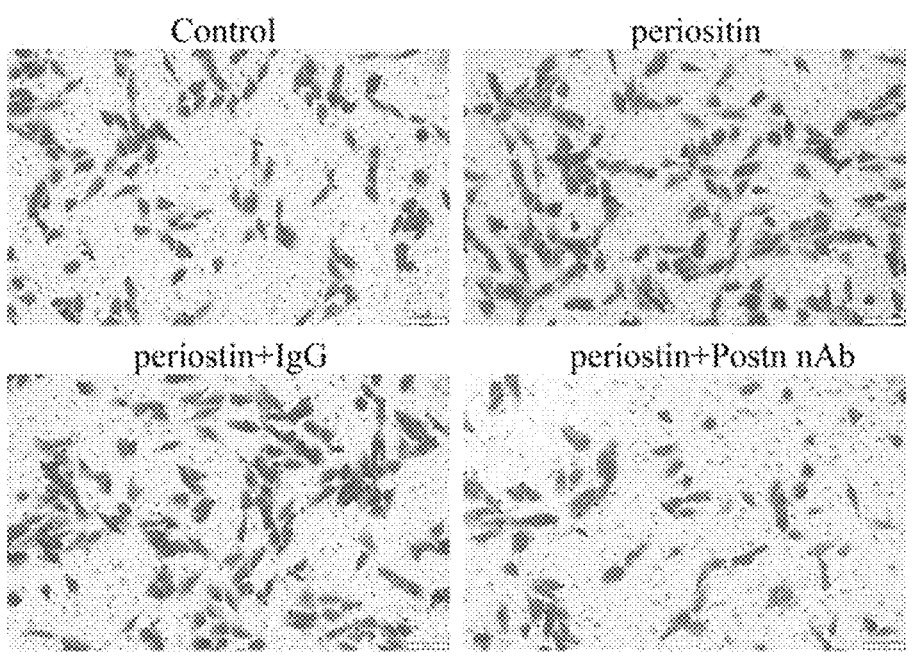
FIG. 12 shows the results of the cell migration assay.
Figure 13:
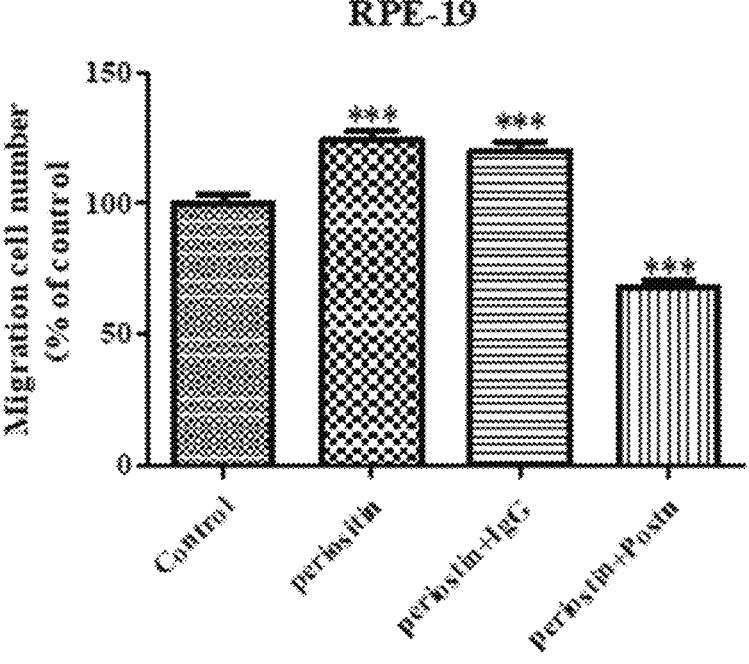
FIG. 13 shows the relative cell migration rate compared to the blank control group.

(6) Cell migration was observed under the microscope (FIG. 12), and 3 random microscope fields were imaged, counted and plotted with the Image J software (FIG. 13).

Experimental results are shown in Table 11.

TABLE 11

| | Migration cell number | | | average | % of control | | | AVERAGE |
|---|---|---|---|---|---|---|---|---|
| Control | 133 | 142 | 139 | 138.00 | 96.38% | 102.90% | 100.72% | 100.00% |
| Periositin | 177 | 168 | 168 | 171.00 | 128.26% | 121.74% | 121.74% | 123.91% |
| Periositin + IgG | 161 | 167 | 170 | 166.00 | 116.67% | 121.01% | 123.19% | 120.29% |
| Periositin + Postn nAb | 94 | 90 | 97 | 93.67 | 38.12% | 65.22% | 70.29% | 67.87% |

As shown in the experimental results, the ratio and number of migrated cells in the periostin-treated group were significantly increased (P<0.001), while those in the periostin+Postn nAb treated group were significantly reduced (P<0.001), both compared to the control group (Control). The periostin+IgG treated group had slightly less cell migration than the periostin-treated group. It demonstrates that the humanized periostin monoclonal antibody is able to inhibit migration of RPE cells induced by periostin.

5.2.2 Cell Invasion Assay

Figure 14:
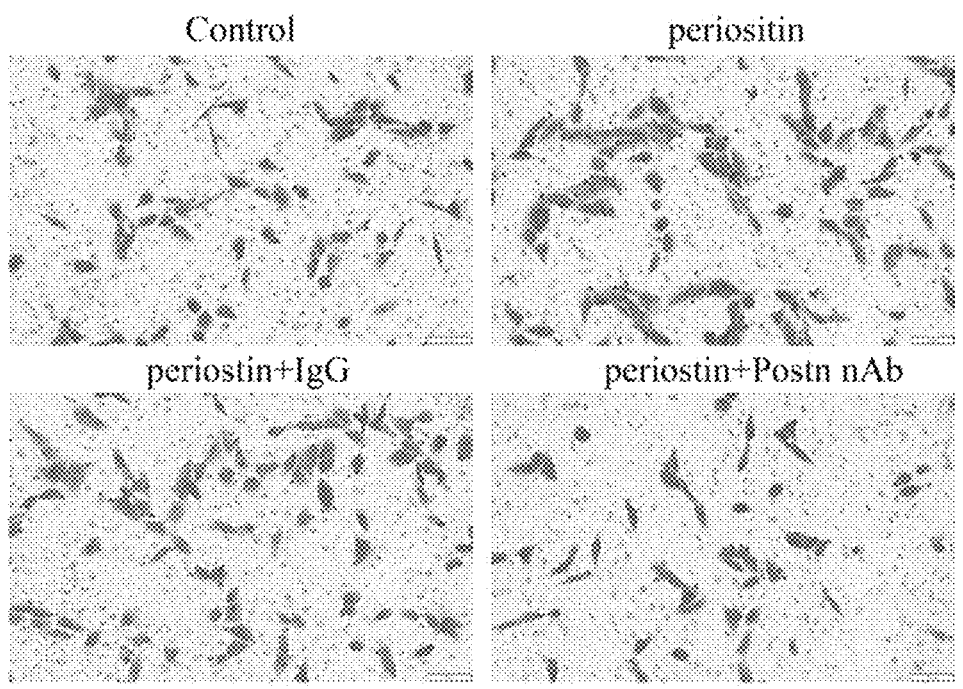
FIG. 14 shows the results of cell invasion assay.
Figure 15:
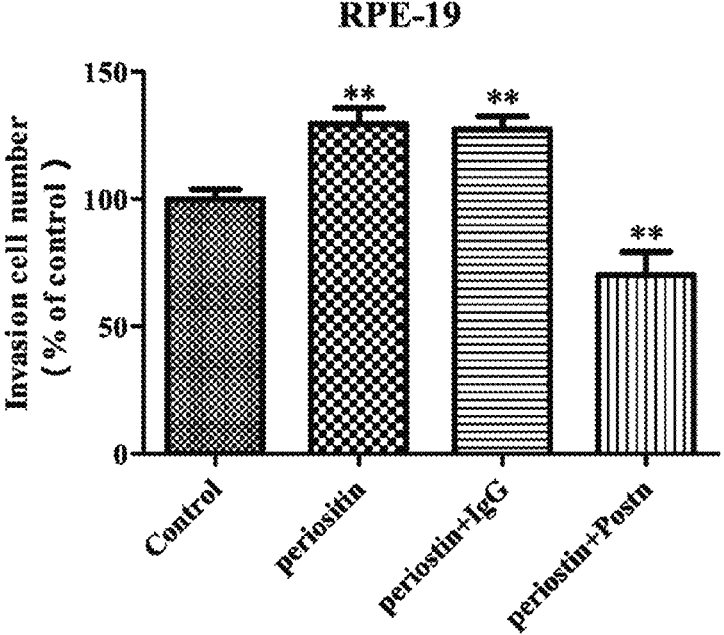
FIG. 15 shows the relative cell invasion rate compared to the blank control group.

The medium containing FBS was added to the lower chamber, and a certain concentration of cell suspension was added to the transwell chamber pre-coated with Matrigel matrix, incubated at 37° C. and 5% $CO_2$ in an incubator for 48 hours, then observed and imaged (FIG. 14). The number of migrated cells was counted (FIG. 15) and results are shown in Table 12.

TABLE 12

| | Invasion cell number | | | Average | % of control | | | AVERAGE |
|---|---|---|---|---|---|---|---|---|
| Control | 78 | 84 | 80 | 80.67 | 96.69% | 104.13% | 99.17% | 100.00% |
| periositin | 100 | 103 | 110 | 104.33 | 123.97% | 127.69% | 136.36% | 129.34% |
| periostin + IgG | 106 | 104 | 98 | 102.67 | 131.40% | 128.93% | 121.49% | 127.27% |
| periostin + Postn nAb | 52 | 65 | 53 | 56.67 | 64.46% | 80.58% | 65.70% | 70.25% |

As shown in the experimental results, compared to the blank control group, the cell migration rate and the number of invasive cells in the periostin-treated group were significantly increased (P<0.01), while that in the periostin+Postn nAb-treated group were significantly reduced (P<0.01). The periostin+IgG treated group had slightly less cell migration than the periostin-treated group. It is showed that the humanized periostin monoclonal antibody has an inhibitive effect on periostin.

5.2.3 Cell Scratch Assay (1) After the cells were grouped as described above, scratches were made using a 10 µl tip vertical to the plate, and the width of each scratch was same as possible.

The cell culture medium was removed, the plate was rinsed with PBS three times to wash away the cell debris resulting from the scratches, and the corresponding serum-free medium was added.

(3) The plate was placed in an incubator and photographed at 0, 6, 24 and 48 hours.

Figure 16:
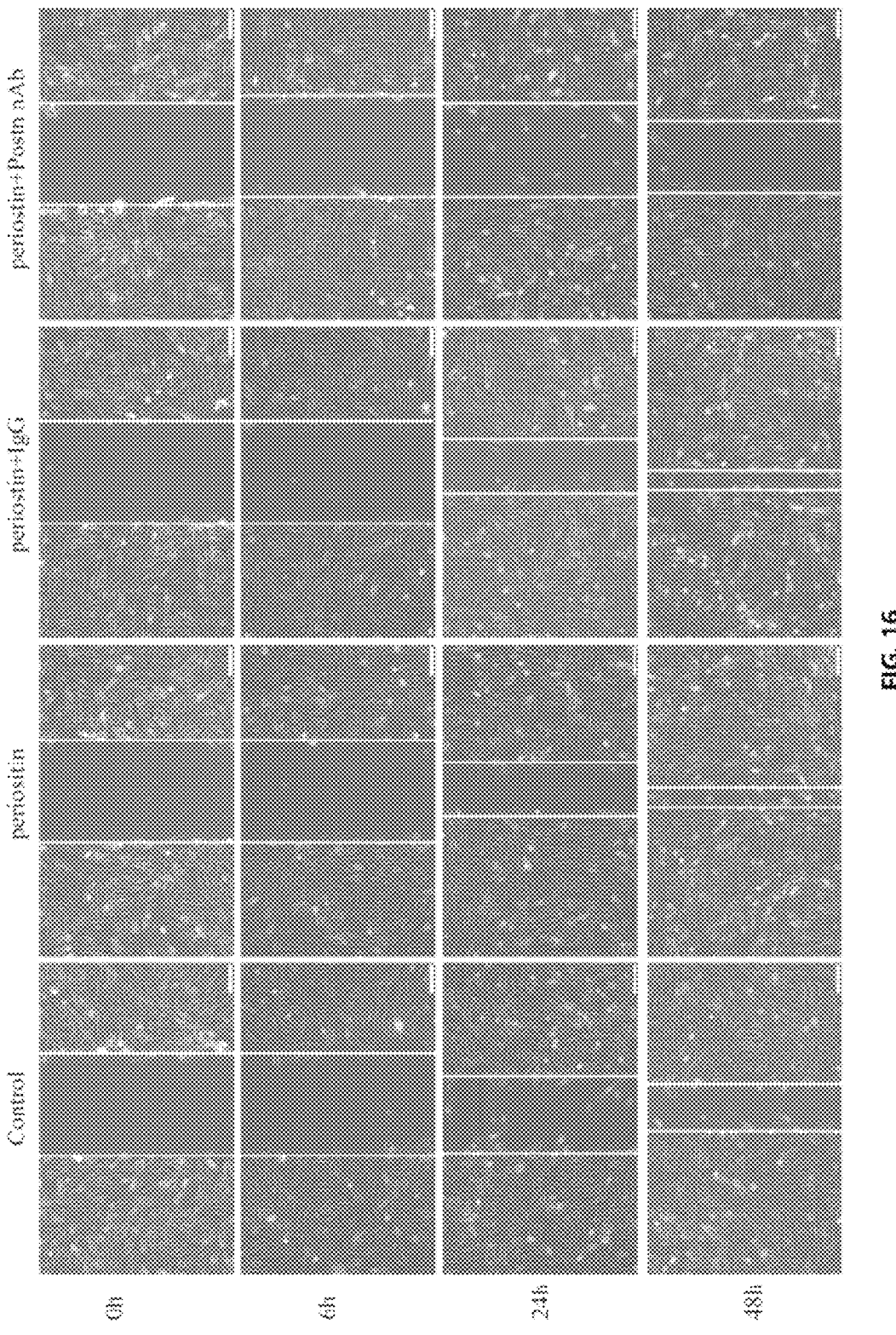
FIG. 16 shows the results of the cell scratch assay.
Figure 17:
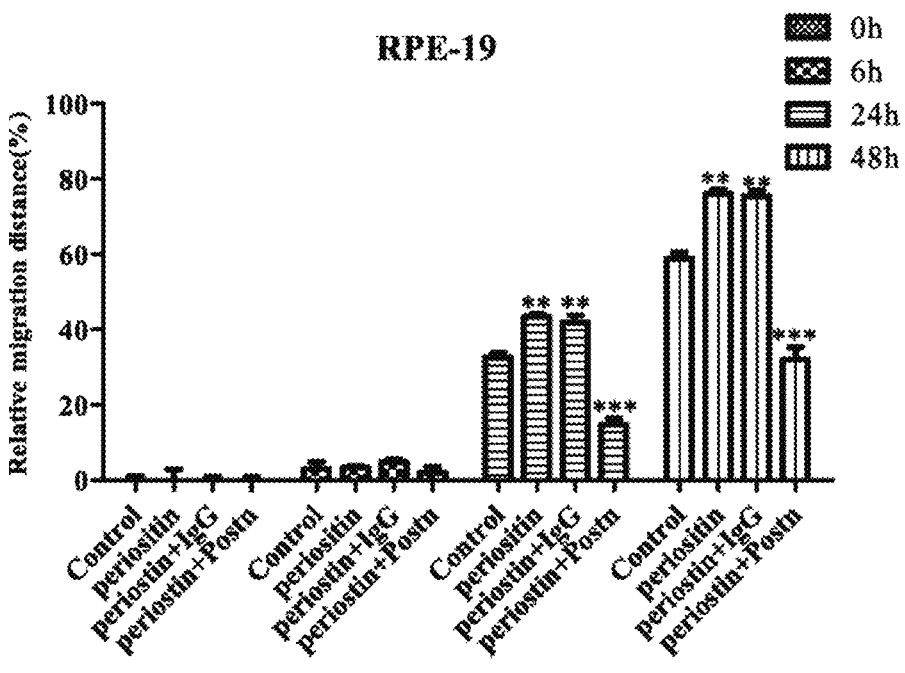
FIG. 17 shows the relative migration distance (%) of cells.

The data collected from pictures were analyzed to obtain experimental results (FIGS. 16-17).

Experimental results and analysis: After the cells were grouped as described above, scratches were made using a 10 μl tip vertical to the plate. The plate was placed in an incubator and photographed at 0, 6, 24 and 48 hours. Results are shown in Table 13 and Table 14.

TABLE 13

| | Distance (μm) | | | | | | | | | | | | |
|---|---|---|---|---|---|---|---|---|---|---|---|---|---|
| | 0 h | | | Average | | 6 h | | | 24 h | | | 48 h | | |
| Control | 368.51 | 358.02 | 370.85 | 365.793 | 359.18 | 341.69 | 362.68 | 243.73 | 240.23 | 256.56 | 138.78 | 159.77 | 153.94 |
| periositin | 377.84 | 368.51 | 342.86 | 363.070 | 353.35 | 352.19 | 347.52 | 201.75 | 205.25 | 209.91 | 88.63 | 78.13 | 94.46 |
| periostin + IgG | 359.18 | 362.68 | 351.02 | 357.627 | 338.19 | 345.19 | 338.19 | 206.41 | 219.24 | 197.08 | 77.3 | 88.63 | 97.79 |
| periostin + Postn nAb | 358.02 | 369.68 | 360.35 | 362.683 | 359.18 | 344.02 | 364.34 | 313.7 | 297.38 | 316.03 | 267.06 | 246.06 | 226.24 |

TABLE 14

| | Relative migration distance (%) | | | | | | | | | | | | |
|---|---|---|---|---|---|---|---|---|---|---|---|---|---|
| | 0 h | | | | 6 h | | | 24 h | | | 48 h | | |
| Control | −0.74% | 2.13% | −1.38% | 1.81% | 6.59% | 0.85% | 33.37% | 34.33% | 29.86% | 62.06% | 56.32% | 57.92% |
| periositin | −4.07% | −1.50% | 5.57% | 2.68% | 3.00% | 4.28% | 44.43% | 43.47% | 42.18% | 75.59% | 78.48% | 73.98% |
| periostin + IgG | −0.43% | −1.41% | 1.85% | 5.43% | 3.48% | 5.43% | 42.28% | 38.70% | 44.89% | 78.39% | 75.22% | 72.66% |
| periostin + Postn nAb | 1.29% | −1.93% | 0.64% | 0.97% | 5.15% | −0.46% | 13.51% | 18.01% | 12.86% | 26.37% | 32.16% | 37.62% |

As shown in the experimental results, at 48 hours, the relative migration distance of the cells in the periostin-treated group was significantly increased (P<0.01), while that in the periostin+Postn nAb-treated group were significantly reduced (P<0.01), both compared to the blank control group. The periostin+IgG treated group had slightly less cell migration than the periostin-treated group. It is showed that the humanized periostin monoclonal antibody has an inhibitive effect on migration of RPE cells induced by periostin.

5.3 Results of Western Blot

The expressions of VEGFA, α-SMA, Col I, Col III and Fibronectin proteins of RPE cells in different groups were detected. Results are shown in Tables 15-19.

VEGFA (vascular endothelial growth factor A) induces angiogenesis and promotes vascular regeneration.

α-SMA (α-Smooth muscle actin) is present in the vascular wall, intestinal mucosal muscularis, muscularis propria, and various tissue mesenchyme, highly expressed in myofibroblasts and myoepithelial cells, and has been shown to increase with increasing fibrosis in studies of organ fibrosis.

Col I (collagen type I) and Col III (collagen type III) promote the proliferation of fibroblasts in the dermis and are closely associated with the wound repair process and the quality of skin injury. They are mainly found in connective tissues such as skin, tendons, ligaments and blood vessels, and are components of the extracellular matrix, which plays a role in supporting the organs and protecting the body, and is also involved in cell attachment and migration.

Fibronectin promotes the growth of adherent cells, affects cell adhesion, cell migration, tumor metastasis, and embryonic development, growth and differentiation, etc.

TABLE 15

| Group | VEGFA | | | GAPDH | | | VEGFA:GAPDH | | | Average | Relative value | | |
|---|---|---|---|---|---|---|---|---|---|---|---|---|---|
| Control | 581015 | 556895 | 602545 | 1053645 | 1075620 | 1035685 | 0.55 | 0.52 | 0.58 | 0.55 | 1.00 | 0.94 | 1.06 |
| periostin | 1082105 | 1036598 | 1125416 | 1030138 | 1012536 | 1053265 | 1.05 | 1.02 | 1.07 | 1.05 | 1.91 | 1.86 | 1.94 |
| periostin + IgG | 1059098 | 992547 | 1076853 | 956898 | 932658 | 986852 | 1.11 | 1.06 | 1.09 | 1.09 | 2.01 | 1.93 | 1.98 |
| periostin + Postn nAb | 381691 | 426452 | 402541 | 1019821 | 998652 | 1036895 | 0.37 | 0.43 | 0.39 | 0.40 | 0.68 | 0.78 | 0.71 |

TABLE 16

| Group | α-SMA | | | GAPDH | | | α-SMA:GAPDH | | | Average | Relative value | | |
|---|---|---|---|---|---|---|---|---|---|---|---|---|---|
| Control | 519129 | 536588 | 557410 | 1053645 | 1075620 | 1035685 | 0.49 | 0.50 | 0.54 | 0.51 | 0.97 | 0.98 | 1.06 |
| periostin | 917194 | 938752 | 897452 | 1030138 | 1012536 | 1053265 | 0.89 | 0.93 | 0.85 | 0.89 | 1.75 | 1.82 | 1.67 |
| periostin + IgG | 873202 | 845685 | 901254 | 956898 | 932658 | 986852 | 0.91 | 0.91 | 0.91 | 0.91 | 1.79 | 1.78 | 1.79 |
| periostin + Postn nAb | 320513 | 302125 | 356420 | 1019821 | 998652 | 1036895 | 0.31 | 0.30 | 0.34 | 0.32 | 0.62 | 0.59 | 0.67 |

TABLE 17

| Group | ColI | | | GAPDH | | | Col:GAPDH | | | Average | Relative value | | |
|---|---|---|---|---|---|---|---|---|---|---|---|---|---|
| Control | 501679 | 535627 | 545896 | 1053645 | 1075620 | 1035685 | 0.48 | 0.50 | 0.53 | 0.50 | 0.95 | 1.00 | 1.05 |
| periostin | 847771 | 865986 | 893568 | 1030138 | 1012536 | 1053265 | 0.82 | 0.86 | 0.85 | 0.84 | 1.64 | 1.71 | 1.70 |
| periostin + IgG | 895815 | 850241 | 876231 | 956898 | 932658 | 986852 | 0.94 | 0.91 | 0.89 | 0.91 | 1.87 | 1.82 | 1.77 |
| periostin + Postn nAb | 298207 | 275410 | 315221 | 1019821 | 998652 | 1036895 | 0.29 | 0.28 | 0.30 | 0.29 | 0.58 | 0.55 | 0.61 |

TABLE 18

| Group | Col III | | | GAPDH | | | Col III:GAPDH | | | Average | Relative value | | |
|---|---|---|---|---|---|---|---|---|---|---|---|---|---|
| Control | 653408 | 685412 | 613154 | 1053645 | 1075620 | 1035685 | 0.62 | 0.64 | 0.59 | 0.62 | 1.01 | 1.03 | 0.96 |
| periostin | 1041617 | 1085265 | 1102458 | 1030138 | 1012536 | 1053265 | 1.01 | 1.07 | 1.05 | 1.04 | 1.64 | 1.74 | 1.70 |
| periostin + gG | 954461 | 975521 | 1003545 | 956898 | 932658 | 986852 | 1.00 | 1.05 | 1.02 | 1.02 | 1.62 | 1.70 | 1.65 |
| periostin + Postn nAb | 399965 | 421352 | 455482 | 1019821 | 998652 | 1036895 | 0.39 | 0.42 | 0.44 | 0.42 | 0.64 | 0.68 | 0.71 |

TABLE 19

| Group | Fibronectin | | | GAPDH | | | Fibronectin:GAPDH | | | Average | Relative value | | |
|---|---|---|---|---|---|---|---|---|---|---|---|---|---|
| Control | 597721 | 622547 | 566214 | 1053645 | 1075620 | 1035685 | 0.57 | 0.58 | 0.55 | 0.56 | 1.01 | 1.03 | 0.97 |
| periostin | 915085 | 936542 | 956223 | 1030138 | 1012536 | 1053265 | 0.89 | 0.92 | 0.91 | 0.91 | 1.57 | 1.64 | 1.61 |
| periostin + IgG | 944392 | 968725 | 923574 | 956898 | 932658 | 986852 | 0.99 | 1.04 | 0.94 | 0.99 | 1.75 | 1.84 | 1.66 |
| periostin + Postn nAb | 337385 | 356854 | 387931 | 1019821 | 998652 | 1036895 | 0.33 | 0.36 | 0.37 | 0.35 | 0.59 | 0.63 | 0.66 |

Figure 18:
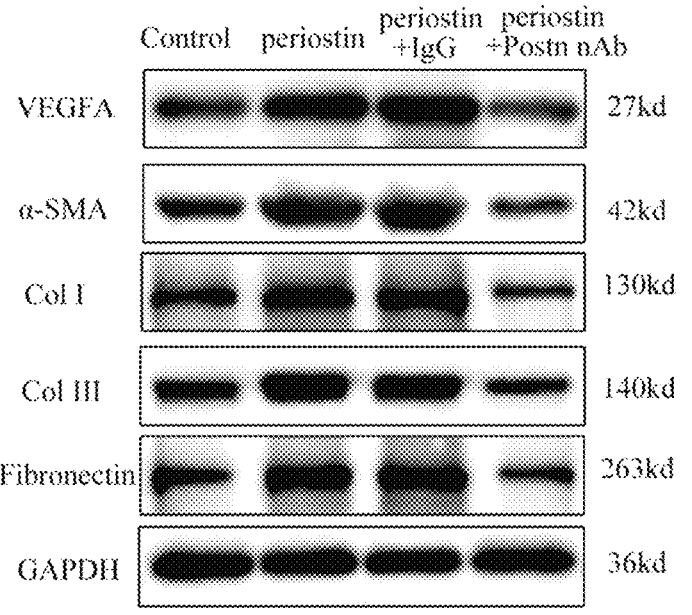
FIG. 18 shows the expression of VEGFA, α-SMA, Col I, Col III and Fibronectin proteins in RPE cells in different groups detected by WB.
Figure 19:
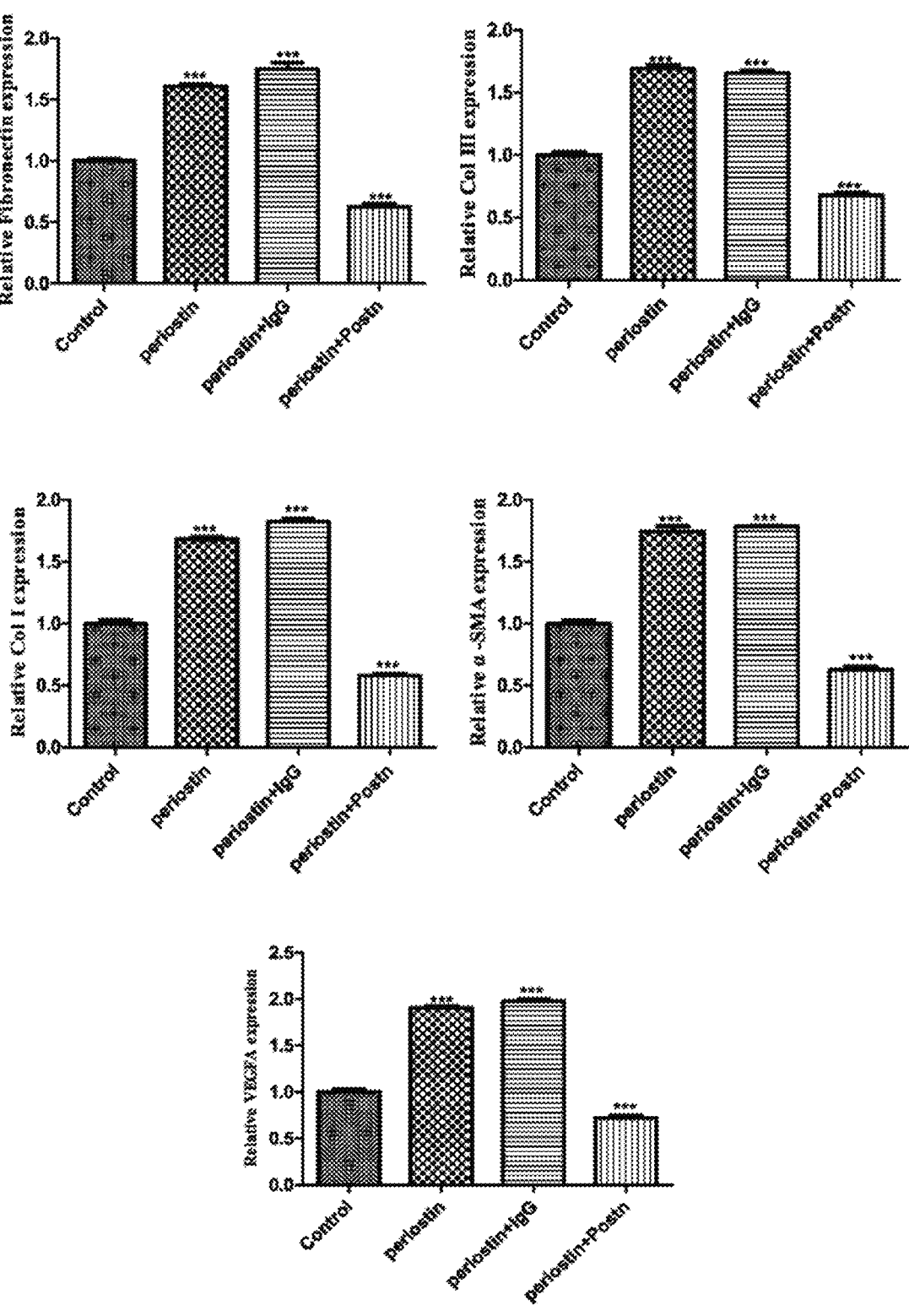
FIG. 19 shows the expression levels of VEGFA, α-SMA, Col I, Col III and Fibronectin proteins in RPE cells in different groups.

As shown in the experimental results (FIGS. 18-19), there are statistically significant difference in the protein expressions between periostin-treated, periostin+IgG treated, and periostin+Postn nAb treated groups and the blank control group (Control) (P<0.001). Compared to the blank control group (Control), the expression of all tested proteins in periostin-treated groups were significantly increased (P<0.001), while the expression of proteins (VEGFA, α-SMA, Col I, Col III and Fibronectin) in periostin+Postn nAb-treated group were all significantly reduced (P<0.001), indicating that periostin monoclonal antibody can inhibit the expression of proteins VEGFA, α-SMA, Col I, Col III, and Fibronectin.

6. Real-Time PCR, WB, and IF Assays for HUVEC Cells In Vitro

Periostin promotes retinal neovascularization and fibrosis through the integrin-focal adhesion kinase (FAK)-phosphatidylinositol 3-kinase (PI3K)-protein kinase B (AKT/PKB) signaling. In order to confirm the therapeutic effect of the humanized periostin monoclonal antibody on vitreoretinal fibrosis, real-time PCR, immunofluorescence and Western blot were used to measure the expression of mRNA and protein of integrin (αvβ3 and αvβ5), vascular endothelial growth factor receptor-2 (VEGFR-2), FAK, PI3K and AKT on the membrane of the human vascular endothelial cells.

The HUVEC cells were cultured in vitro and grouped.

a. Blank control group (Control) (without recombinant periostin protein or antibody)

b. Periostin group (with only periostin protein)

c. Control IgG group (with periostin+control IgG)

d. periostin antibody group (with periostin+Postn nAb)

Postn nAb: the humanized periostin antibody produced by the present invention

Human periostin protein was incubated with human periostin antibody for 1 hour and then added to the cells for 24 hours for the following assays, in which the concentration of control IgG used was the same as that of the humanized anti-periostin monoclonal antibody.

6.1 Real-Time PCR Assay

The mRNA expressions of integrins (αvβ3 and αvβ5), VEGFR-2, FAK, PI3K, p-PI3K, AKT and p-AKT on the membrane of the vascular endothelial cells were measured.

Figure 20:
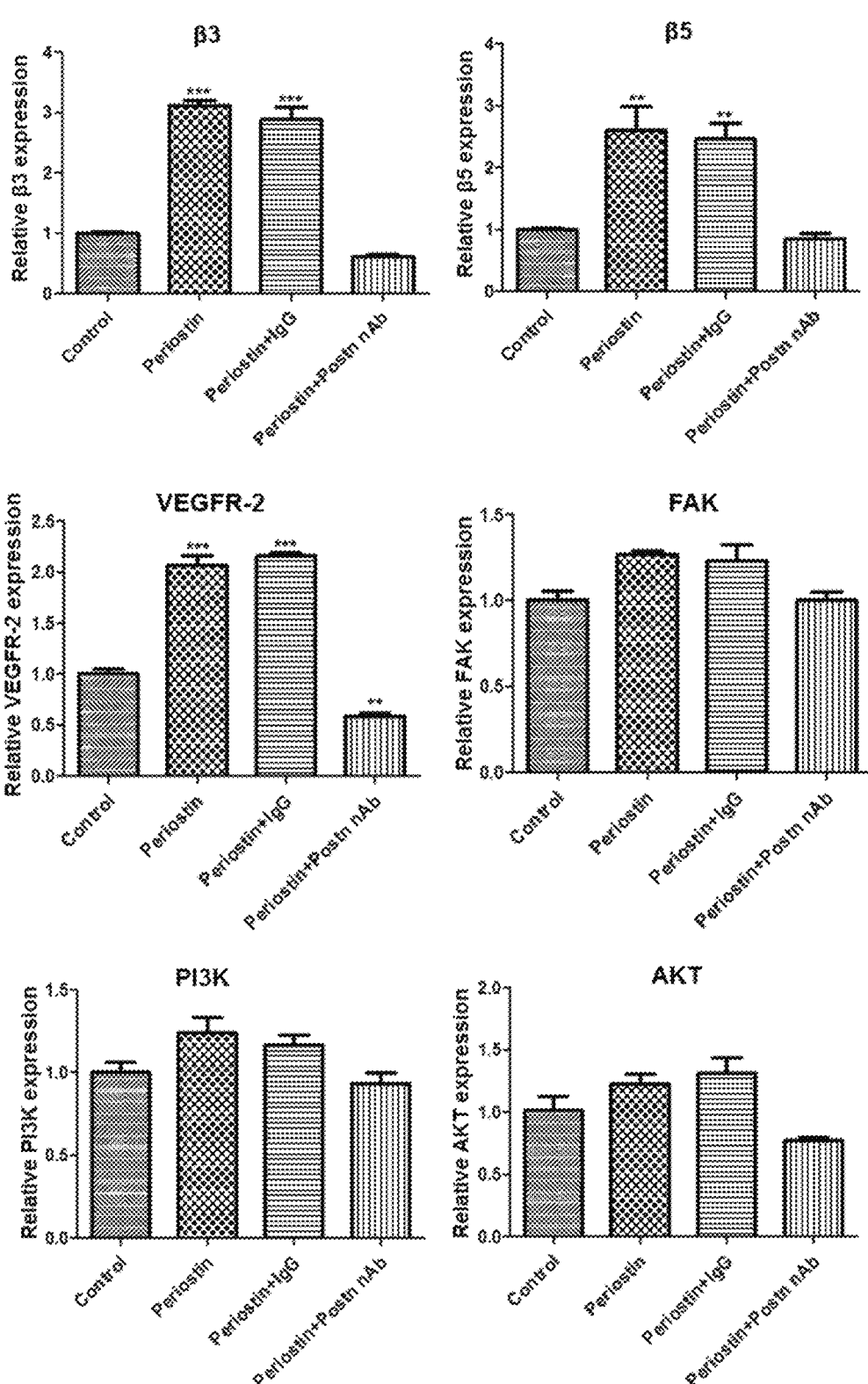
FIG. 20 shows the mRNA expression of αvβ3, αvβ5 integrins, VEGFR-2, FAK, PI3K, p-PI3K, AKT and p-AKT on the membrane of vascular endothelial cells in different groups.

As shown in FIG. 20, compared to the blank control group, the gene expression of αvβ3, αvβ5, VEGFR-2, FAK, PI3K, p-PI3K, AKT and p-AKT in the periostin-treated group were all increased, while those in the periostin+Postn nAb-treated group were all decreased, in particular the mRNA expression of VEGFR-2 was significantly lower than that of the blank control group (P<0.001), indicating that the humanized periostin monoclonal antibody can inhibit the mRNA expression of VEGFR-2, FAK, PI3K, p-PI3K, AKT and p-AKT.

6.2 Detection of Protein Expressions of $\alpha v \beta 3$, $\alpha v \beta 5$, VEGFR-2, FAK, PI3K, p-PI3K, AKT and p-AKT in HUVEC Cells by Western Blot Normal cultured HUVEC cells were plated at $10^6$ cells/dish (6 cm dish) and cultured at 5% $CO_2$, 37° C., overnight. After adhesion, the cells were treated according to the grouping. Total protein was subjected to content detection using the BCA kit, SDS-PAGE, followed by membrane transferring, blocking with blocking buffer, washing, incubating with the primary antibody overnight in a refrigerator at 4° C., washing, incubating with the secondary antibody at room temperature on a shaker for 1 hour, and performing color development. The gray-scale value ratio of the tested proteins to the reference protein under the same conditions in each group was used as the relative expression of the tested proteins.

Figure 21:
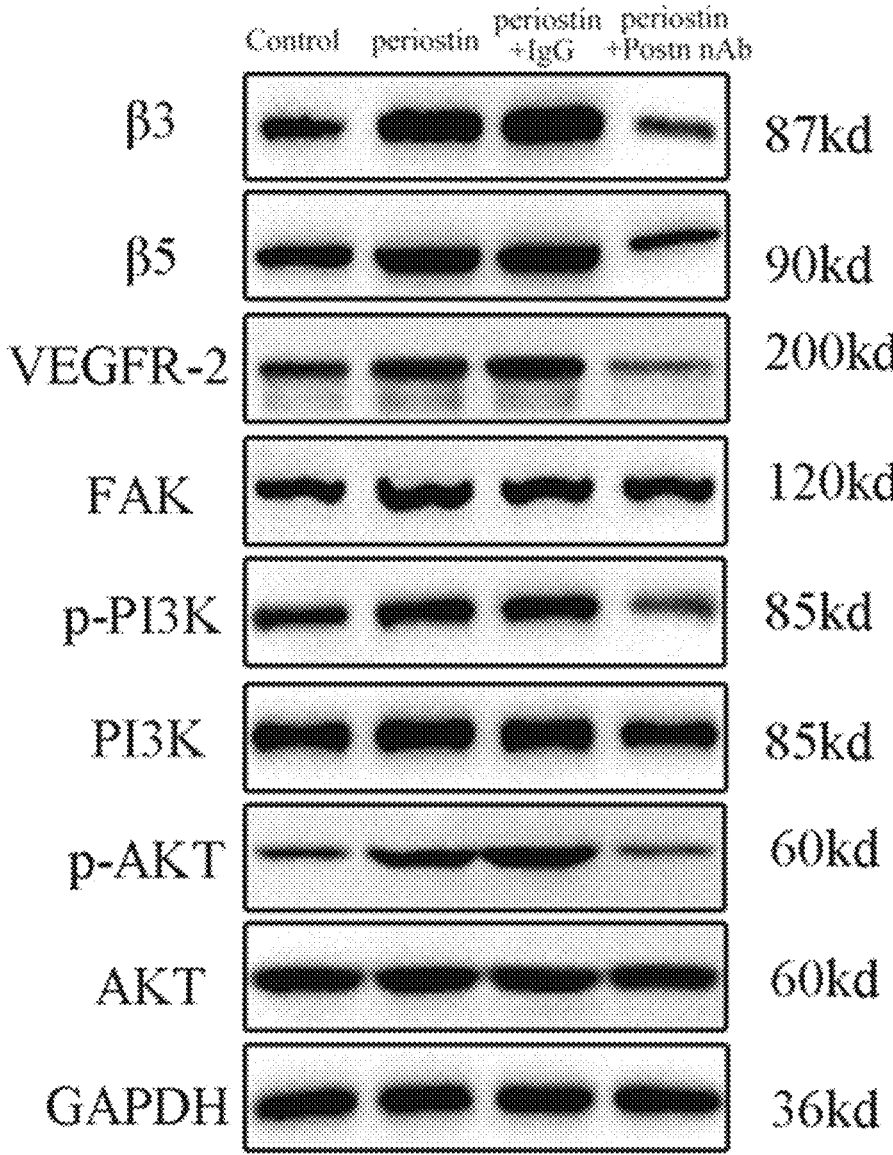
FIG. 21 shows the Western blot results of the tested proteins in HUVEC cells in different groups.
Figure 22:
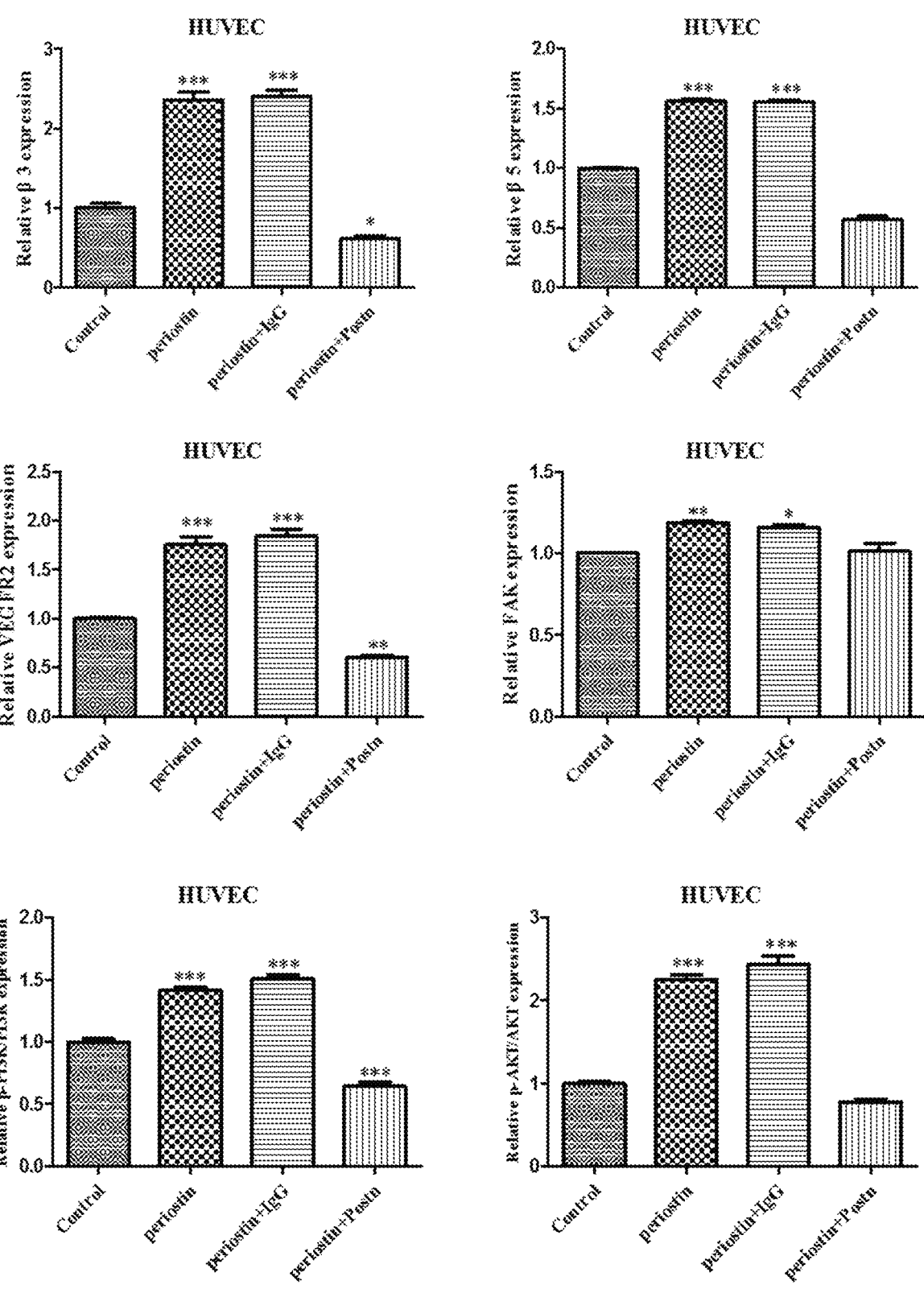
FIG. 22 shows the expression levels of tested proteins in HUVEC cells in different groups.
Figure 23:
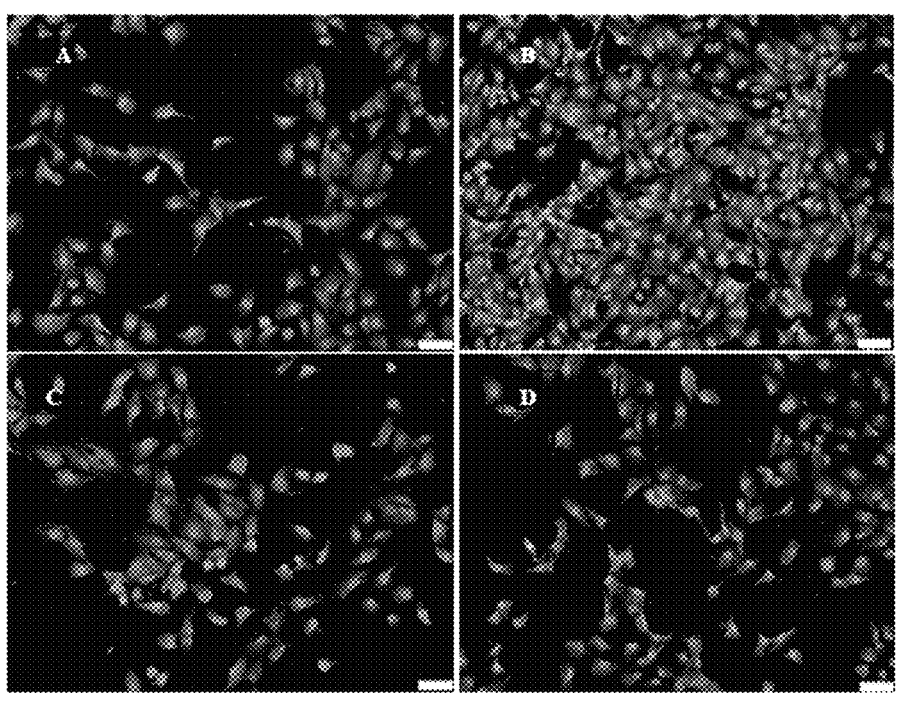
FIG. 23 shows the expression of FAK protein in HUVEC cells detected by IF.
Figure 24:
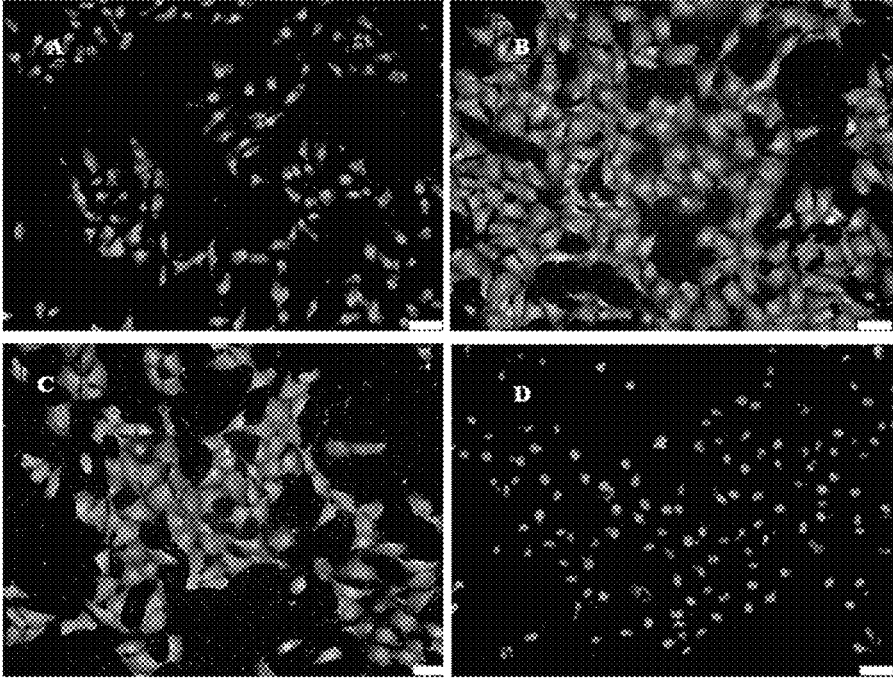
FIG. 24 shows the expression of VEGFR2 protein in HUVEC cells detected by IF.
Figure 25:
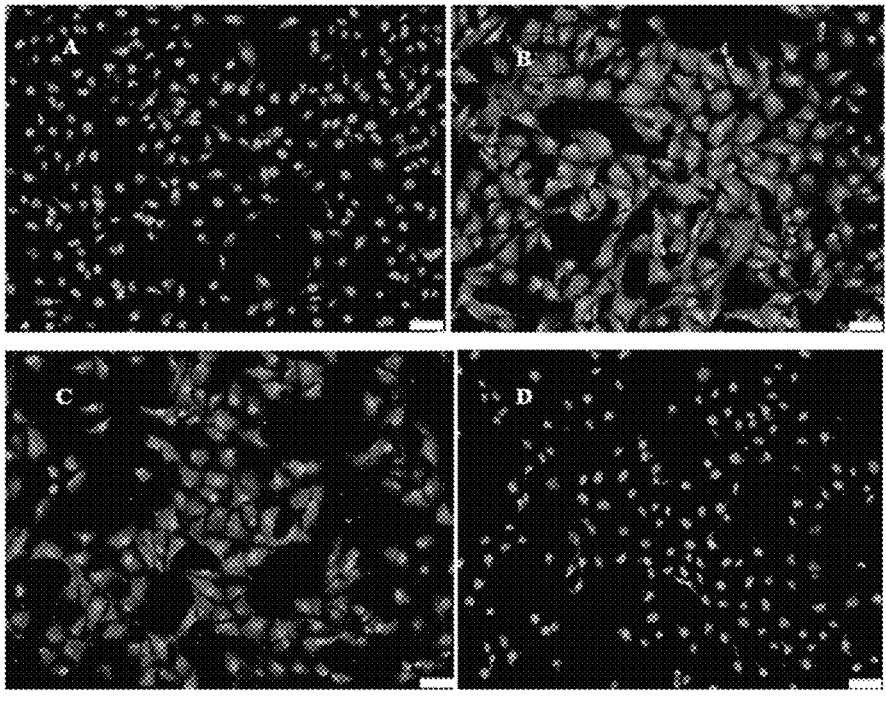
FIG. 25 shows the expression of αvβ3 protein in HUVEC cells detected by IF.
Figure 26:
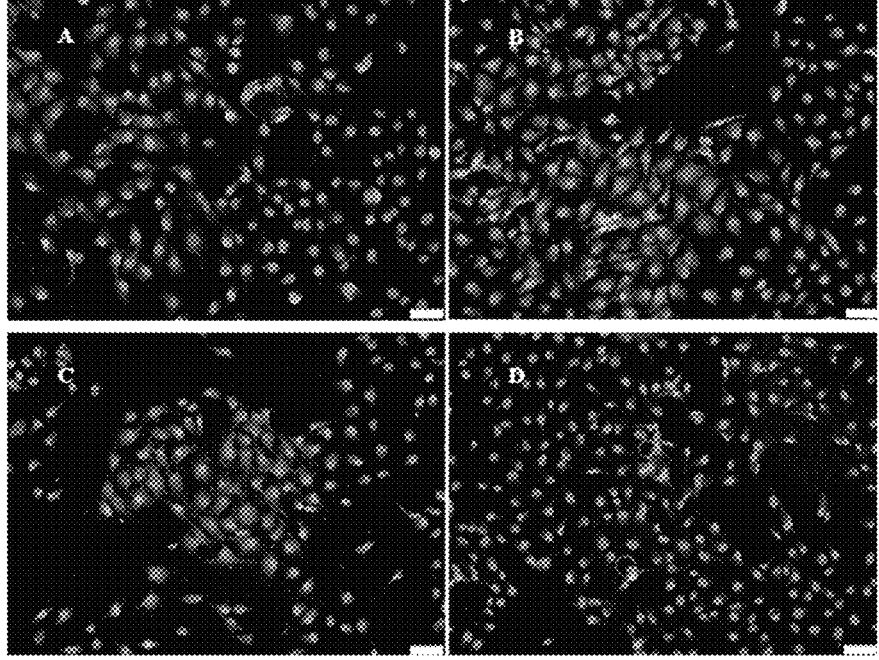
FIG. 26 shows the expression of αvβ5 protein in HUVEC cells detected by IF.

The expression and grey scale analysis of proteins in HUVEC cells of different groups are shown in FIGS. 21-22. As shown in the experimental results, compared to the blank control group, the expressions of $\alpha v \beta 3$, $\alpha v \beta 5$, VEGFR-2, FAK, PI3K, p-PI3K, AKT and p-AKT in the periostin-treated group were increased, while those in the periostin+Postn nAb treated group were reduced. The expression of these protein in the periostin+Postn nAb treated group were all lower than those in periostin treated group, indicating that the humanized periostin monoclonal antibody has an inhibitive effect on periostin.

6.3 Detection of the Expression of Protein $\alpha v \beta 3$, $\alpha v \beta 5$, VEGFR-2 and FAK in HUVEC Cells by IF The coverslips where cells had grew were washed with PBS in the culture plate, fixed with 4% paraformaldehyde, permeabilized with 0.5% Triton X-100 for 20 minutes at room temperature. The coverslips were incubated with primary antibody in wet box at 4° C. overnight and then incubated with fluorescent secondary antibody in wet box at 20-37° C. for 1 hour. The cell nuclei were counterstained by dropwise addition of DAPI, and the coverslips were mounted and observed under fluorescence microscope (FIGS. 23-26).

Under the fluorescence microscopy, it was seen that periostin protein was expressed in the cytoplasm of HUVEC cells. $\alpha v \beta 3$, $\alpha v \beta 5$, VEGFR-2 and FAK showed weak fluorescence in the cell cytoplasm in the blank control group and strong fluorescence in the periostin-treated group. The fluorescence signals of the cells in the periostin+Postn nAb-treated group were significantly weaker than those in the periostin-treated group, and were no statistically significant compared to those in the blank control group, indicating that the humanized periostin monoclonal antibody can inhibit the action of periostin by blocking the integrin-FAK-PI3K-AKT/PKB signaling, thereby inhibiting retinal fibrosis.

The above embodiments are only preferred embodiments of the present invention. It should be noted that, for those skilled in the art, other improvements and modifications may be further made without departing from the principle of the present invention, and these improvements and modifications should also be deemed as falling into the protection scope of the present invention.

---

The invention claimed is:

1. A humanized anti-periostin monoclonal antibody comprising a heavy chain variable region and a light chain variable region, wherein the heavy chain variable region comprises the amino acid sequence set forth in SEQ ID NO: 1, and the light chain variable region comprises the amino acid sequence set forth in SEQ ID NO: 2.

2. The humanized anti-periostin monoclonal antibody according to claim 1, which comprises a heavy chain constant region and a light chain constant region, wherein the heavy chain constant region is a heavy chain constant region of human IgG1, and the light chain constant region is a light chain constant region of kappa chain.

3. The humanized anti-periostin monoclonal antibody according to claim 1, which comprises a heavy chain and a light chain, wherein the amino acid sequence of the heavy chain is set forth in SEQ ID NO: 3, and the amino acid sequence of the light chain is set forth in SEQ ID NO: 4.

4. A nucleic acid encoding the humanized anti-periostin monoclonal antibody according to claim 1.

5. The nucleic acid according to claim 4, wherein the sequence of the nucleic acid encoding the heavy chain of the humanized anti-periostin monoclonal antibody is SEQ ID NO: 5, and the sequence of the nucleic acid encoding the light chain of the humanized anti-periostin monoclonal antibody is SEQ ID NO: 6.

6. The nucleic acid according to claim 5, wherein the sequence of the nucleic acid encoding the heavy chain of the humanized anti-periostin monoclonal antibody is SEQ ID NO: 7, and the sequence of the nucleic acid encoding the light chain of the humanized anti-periostin monoclonal antibody is SEQ ID NO: 8.

7. An expression vector comprising the nucleic acid according to claim 4.

8. The expression vector according to claim 7, wherein a backbone vector of the expression vector is PATX-GS2.

9. A host cell transformed or transfected with the expression vector according to claim 8.

10. A method for producing the humanized anti-periostin monoclonal antibody according to claim 1, comprising culturing a host cell transformed or transfected with an expression vector comprising a nucleic acid encoding the humanized anti-periostin monoclonal antibody and inducing the expression of the humanized anti-periostin monoclonal antibody.

11. A medicament for the treatment of tissue fibrosis and/or a malignant tumor, comprising the humanized anti-periostin monoclonal antibody according to claim 1.

12. A kit for diagnosing tissue fibrosis and/or a malignant tumor, comprising the humanized anti-periostin monoclonal antibody according to claim 1.

* * * * *

SEQUENCE LISTING

```
Sequence total quantity: 38
SEQ ID NO: 1                moltype = AA  length = 117
FEATURE                     Location/Qualifiers
source                      1..117
                            mol_type = protein
                            organism = synthetic construct
SEQUENCE: 1
EVQLVQSGAE VKKPGESLKI SCKASGYSFT DYFMNWVRQM PGKGLEWIGR INPYSGDTLY   60
NQRLQGQVTL SADKSISTAY LQLSSLKASD TAMYYCGRSG VSGLDYWGQG TLVTVSS      117

SEQ ID NO: 2                moltype = AA  length = 106
FEATURE                     Location/Qualifiers
source                      1..106
                            mol_type = protein
                            organism = synthetic construct
SEQUENCE: 2
DIQLTQSPSS LSASVGDRVT ITCSASSSAS YMHWYQQKPG KAPKNWIYDT SKLASGVPSR   60
FSGSGSGTDY TLTISSLQPE DAATYYCQQW SSNPPTFGGG TKVEIK                  106

SEQ ID NO: 3                moltype = AA  length = 466
FEATURE                     Location/Qualifiers
source                      1..466
                            mol_type = protein
                            organism = synthetic construct
SEQUENCE: 3
MKHLWFFLLL VAAPRWVLSE VQLVQSGAEV KKPGESLKIS CKASGYSFTD YFMNWVRQMP   60
GKGLEWIGRI NPYSGDTLYN QRLQGQVTLS ADKSISTAYL QLSSLKASDT AMYYCGRSGV   120
SGLDYWGQGT LVTVSSASTK GPSVFPLAPS SKSTSGGTAA LGCLVKDYFP EPVTVSWNSG   180
ALTSGVHTFP AVLQSSGLYS LSSVVTVPSS SLGTQTYICN VNHKPSNTKV DKKVEPKSCD   240
KTHTCPPCPA PELLGGPSVF LFPPKPKDTL MISRTPEVTC VVVDVSHEDP EVKFNWYVDG   300
VEVHNAKTKP REEQYNSTYR VVSVLTVLHQ DWLNGKEYKC KVSNKALPAP IEKTISKAKG   360
QPREPQVYTL PPSREEMTKN QVSLTCLVKG FYPSDIAVEW ESNGQPENNY KTTPPVLDSD   420
GSFFLYSKLT VDKSRWQQGN VFSCSVMHEA LHNHYTQKSL SLSPGK                  466

SEQ ID NO: 4                moltype = AA  length = 233
FEATURE                     Location/Qualifiers
source                      1..233
                            mol_type = protein
                            organism = synthetic construct
```

```
SEQUENCE: 4
MVLQTQVFIS LLLWISGAYG DIQLTQSPSS LSASVGDRVT ITCSASSSAS YMHWYQQKPG   60
KAPKNWIYDT SKLASGVPSR FSGSGSGTDY TLTISSLQPE DAATYYCQQW SSNPPTFGGG  120
TKVEIKRTVA APSVFIFPPS DEQLKSGTAS VVCLLNNFYP REAKVQWKVD NALQSGNSQE  180
SVTEQDSKDS TYSLSSTLTL SKADYEKHKV YACEVTHQGL SSPVTKSFNR GEC          233

SEQ ID NO: 5              moltype = DNA   length = 1401
FEATURE                  Location/Qualifiers
source                   1..1401
                         mol_type = other DNA
                         organism = synthetic construct
SEQUENCE: 5
atgaagcacc tgtggttctt cctgctgctg gtggctgctc ctaggtgggt gctgagcgag   60
gtgcagctgg tgcagagcgg cgccgaggtg aagaagcccg gcgagagcct gaagatctcc  120
tgtaaggctt ccggctactc cttcaccgac tactttatga attgggtgcg gcagatgccc  180
ggcaagggcc tggagtggat cggcagaatc aatccttaca gcggcgacac cctgtacaac  240
cagcggctgc agggccaggt gaccctgtcc gctgataaga gcatctccac cgcctacctg  300
cagctgtcct ccctgaaggc ctccgacacc gccatgtact actgggcag gagcggcgtg  360
agcggcctgg actactgggg ccagggcacc ctggtgaccg tgagcagcgc tagcaccaag  420
ggaccttctg tgttccctct ggctccttct tctaagtcca cttccggtgg tacagcagct  480
ctgggttgtc tggtgaagga ttacttccca gaaccagtga ctgtgtcctg gaactccgga  540
gctctgactt ctggagtgca tactttccca gcagtgctga atctagcgg actgtactct  600
ctgtcttccg tggtgactgt gccttcttct ccctgggga ctcaaactta catctgcaac  660
gtgaaccaca gccctccaa caccaaggtg gacaagaagg tggagccaaa gagctgcgat  720
aagacccaca cctgtccacc ttgtccagct ccagaactgc tgggtgggcc ttctgtgttt  780
ctgttcccac ctaagccaaa ggataccctg atgatctct ggacccccga agtgacctgt  840
gtggtcgtcg atgtgtctca tgaagaccct gaagtgaagt tcaactggta cgtggacggc  900
gtggaagtgc ataacgcaaa gaccaagccc agggaagagc aatacaactc cacctacagg  960
gtggtctccg tcctgacagt cctgcatcag gattggctga acggcaagga gtacaagtgc 1020
aaggtctcca ataaagccct gcctgcccct atcgagaaaa ccattagcaa agccaaggcc 1080
cagcccaggg agccccaggt ctatacactg cccccccagca gggaggagat gacaaaaaat 1140
caggtcagcc tgacatgcct ggtcaaaggc ttttatccca gcgacattgc cgtcgagtgg 1200
gagtccaatg gccagcccga gaataattat aaaacaacac ccccgtcct ggacagcgac 1260
ggcagctttt ttctgtatag caaactgaca gtcgataaaa gcaggtggca gcaggcaat 1320
gtcttttcct gcagcgtcat gcacgaggcc ctgcacaatc actatactca gaaaagcctg 1380
agcctgtccc ccgggaaatg a                                            1401

SEQ ID NO: 6              moltype = DNA   length = 702
FEATURE                  Location/Qualifiers
source                   1..702
                         mol_type = other DNA
                         organism = synthetic construct
SEQUENCE: 6
atggtgctgc agacccaggt gtttatcagc ctgctgctgt ggatcagcgg cgcttacggc   60
gacatccagc tgacccagtc cccctccagc ctgagcgcta gcgtgggcga ccgggtgacc  120
atcacctgct ccgcctccag ctccgccagc tacatgcact ggtaccagca gaagcccggc  180
aaggcccca agaactggat ctatgatacc agcaagctgg ccagcggcgt gcccagcaga  240
ttcagcggca gcggctccgg caccgattac accctgacca tcagctccct gcagcccgag  300
gatgctgcca cctactactg ccagcagtgg tcctccaacc cccctacctt tggcggcggc  360
accaaggtgg agatcaagcg tacggtggct gcaccttctg tgttcatctt ccctccatct  420
gatgagcagc tgaagtctgg aaccgcatct gtcgtctgtc tgctgaacaa cttttaccct  480
agggaggcta aggtccaatg gaaggtggac aacgccctgc agtctggtaa tagccaggaa  540
agcgtgaccg aacaggattc caaggactcc acctactccc tgtcctccac actgacactg  600
agcaaagccc actatgaaaa gcacaaagtg tatgcctgcg aggtcactca tcagggcctg  660
tccagcccg tgactaaaag ctttaatagg ggggagtgct ga                      702

SEQ ID NO: 7              moltype = DNA   length = 1424
FEATURE                  Location/Qualifiers
source                   1..1424
                         mol_type = other DNA
                         organism = synthetic construct
SEQUENCE: 7
gaattcgccg ccaccatgaa gcacctgtgg ttcttcctgc tgctggtggc tgctcctagg   60
tgggtgctga gcgaggtgca gctggtgcag agcggcgccg aggtgaagaa gcccggcgag  120
agcctgaaga tctcctgtaa ggcttccggc tactccttca ccgactactt tatgaattgg  180
gtgcggcaga tgcccggcaa gggcctggag tggatcggca gaatcaatcc ttacagcggc  240
gacaccctgt acaaccagcg gctgcagggc caggtgaccc tgtccgctga taagagcatc  300
tccaccgcct acctgcagct gtcctccctg aaggcctccg acaccgccat gtactactgt  360
ggcaggagcg gcgtgagcgg cctggactac tggggccagg gcaccctggt gaccgtgagc  420
agcgctagca ccaagggacc ttctgtgttc cctctggctc cttcttctaa gtccacttcc  480
ggtggtacag cagctctggg ttgtctggtg aaggattact tcccagaacc agtgactgtg  540
tcctggaact ccggagctct gacttctgga gtgcatactt tccagcagt gctgcaatct  600
agcggactgt actctctgtc ttccgtggtg actgtgcctt cttcccct gggactcaa  660
acttacatct gcaacgtgaa ccacagcccc tccaacacca aggtggacaa gaaggtgcac  720
ccaaagagct gcgataagac ccacacctgt ccaccttgtc cagctccaga actgctgggt  780
gggccttctg tgtttctgtt cccacctaag ccaaaggata ccctgatgat ctctaggacc  840
ccagaagtga cctgtgtggt cgtcgatgtg tctcatgaag accctgaagt gaagttcaac  900
tggtacgtgg acggggtgga agtgcataac gcaaagacca gcccaggga gagcaatac  960
aactccacct acagggtggt ctccgtcctg acagtcctgc atcaggattg gctgaacggc 1020
```

-continued

```
aaggagtaca agtgcaaggt ctccaataaa gccctgcctg cccctatcga gaaaaccatt   1080
agcaaagcca aaggccagcc cagggagccc caggtctata cactgccccc cagcaggggag  1140
gagatgacaa aaaatcaggt cagcctgaca tgcctggtca aaggctttta tcccagcgac   1200
attgccgtcg agtgggagtc caatggccag cccgagaata attataaaac aacacccccc   1260
gtcctggaca gcgacggcag cttttttctg tatagcaaac tgacagtcga taaaagcagg   1320
tggcagcagg gcaatgtctt ttcctgcagc gtcatgcacg aggccctgca caatcactat   1380
actcagaaaa gcctgagcct gtcccccggg aaatgagcgg ccgc                    1424
```

SEQ ID NO: 8          moltype = DNA  length = 725
FEATURE                Location/Qualifiers
source                1..725
                        mol_type = other DNA
                        organism = synthetic construct
SEQUENCE: 8

```
gaattcgccg ccaccatggt gctgcagacc caggtgttta tcagcctgct gctgtggatc   60
agcggcgctt acggcgacat ccagctgacc cagtccccct ccagcctgag cgctagcgtg  120
ggcgaccggg tgaccatcac ctgctccgcc tccagctccg ccagctacat gcactggtac  180
cagcagaagc ccggcaaggc ccccaagaac tggatctatg ataccagcaa gctggccagc  240
ggcgtgccca gcagattcag cggcagcggc tccggcaccg attacaccct gaccatcagc  300
tccctgcagc ccgaggatgc tgccacctac tactgccagc agtggtcctc caacccccct  360
acctttggcg gcgcaccaa ggtggagatc aagcgtacgg tggctgcacc ttctgtgttc   420
atcttccctc catctgatga gcagctgaag tctggaaccg catctgtcgt ctgtctgctg  480
aacaactttt accccaggga ggctaaggtc caatggaagg tggacaacgc cctgcagtct  540
ggtaatagcc aggaaagcgt gaccgaacag gattccaagg actccaccta ctccctgtcc  600
tccacactga cactgagcaa agccgactat gaaaagcaca agtgtatgc ctgcgaggtc   660
actcatcagg gcctgtccag ccccgtgact aaaagcttta ataggggga gtgctgagcg   720
gccgc                                                              725
```

SEQ ID NO: 9          moltype = AA  length = 330
FEATURE                Location/Qualifiers
source                1..330
                        mol_type = protein
                        organism = synthetic construct
SEQUENCE: 9

```
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                    330
```

SEQ ID NO: 10         moltype = AA  length = 107
FEATURE                Location/Qualifiers
source                1..107
                        mol_type = protein
                        organism = synthetic construct
SEQUENCE: 10

```
RTVAAPSVFI FPPSDEQLKS GTASVVCLLN NFYPREAKVQ WKVDNALQSG NSQESVTEQD   60
SKDSTYSLSS TLTLSKADYE KHKVYACEVT HQGLSSPVTK SFNRGEC                 107
```

SEQ ID NO: 11         moltype = AA  length = 19
FEATURE                Location/Qualifiers
source                1..19
                        mol_type = protein
                        organism = synthetic construct
SEQUENCE: 11

```
MKHLWFFLLL VAAPRWVLS                                                19
```

SEQ ID NO: 12         moltype = AA  length = 20
FEATURE                Location/Qualifiers
source                1..20
                        mol_type = protein
                        organism = synthetic construct
SEQUENCE: 12

```
MVLQTQVFIS LLLWISGAYG                                               20
```

SEQ ID NO: 13         moltype = AA  length = 106
FEATURE                Location/Qualifiers
source                1..106
                        mol_type = protein
                        organism = synthetic construct
SEQUENCE: 13

```
DIVLTQSPAI MSASPGDKVT MTCSASSSAS YMHWYQQKSG TSPKRWIYDT SKLASGVPAR   60
FSGSGSGTSY SLTISSMEAE DAATYYCQQW SSNPPTFGGG TKLEIK                  106
```

SEQ ID NO: 14         moltype = AA  length = 106
FEATURE                Location/Qualifiers
source                1..106
                        mol_type = protein -continued

```
                        organism = synthetic construct
SEQUENCE: 14
QIVLTQSPVI MSASPGDKVT MTCSASSSAS YMHWYQQKSG TSPKRWIYDT SKLASGVPAR   60
FSGSGSGTSY SLTISSMEAE DAATYYCQQW SSNPPTFGGG TKLEIK               106

SEQ ID NO: 15         moltype = AA  length = 117
FEATURE               Location/Qualifiers
source                1..117
                      mol_type = protein
                      organism = synthetic construct
SEQUENCE: 15
EVQLQQSGPE LVKPGASVRI SCKASGYSFT DYFMNWVKQS HGRSLEWIGR INPYSGDTLY   60
NQRLKGKATL TVDKSSSTAH MELLSLTSED SAVYYCGRSG VSGLDYWGQG TSVTVSS     117

SEQ ID NO: 16         moltype = AA  length = 5
FEATURE               Location/Qualifiers
source                1..5
                      mol_type = protein
                      organism = synthetic construct
SEQUENCE: 16
SSASY                                                                5

SEQ ID NO: 17         moltype = AA  length = 9
FEATURE               Location/Qualifiers
source                1..9
                      mol_type = protein
                      organism = synthetic construct
SEQUENCE: 17
QQWSSNPPT                                                            9

SEQ ID NO: 18         moltype = AA  length = 8
FEATURE               Location/Qualifiers
source                1..8
                      mol_type = protein
                      organism = synthetic construct
SEQUENCE: 18
GYSFTDYF                                                             8

SEQ ID NO: 19         moltype = AA  length = 8
FEATURE               Location/Qualifiers
source                1..8
                      mol_type = protein
                      organism = synthetic construct
SEQUENCE: 19
INPYSGDT                                                             8

SEQ ID NO: 20         moltype = AA  length = 10
FEATURE               Location/Qualifiers
source                1..10
                      mol_type = protein
                      organism = synthetic construct
SEQUENCE: 20
GRSGVSGLDY                                                          10

SEQ ID NO: 21         moltype = DNA  length = 1424
FEATURE               Location/Qualifiers
source                1..1424
                      mol_type = other DNA
                      organism = synthetic construct
SEQUENCE: 21
gaattcgccg ccaccatgaa gcacctgtgg tttttcctgc tgctggtggc cgcccccagg   60
tgggttctgt cccaggtgca gctggtgcag agcggcgccg aggtgaagaa gcctggcgct  120
tccgtgaagg tgtcctgcaa ggcttctggc tatagcttta ccgattattt catgaactgg  180
gtgcggcagg ctcctggcca gggcttggag tggatcaacc ttactccggc              240
gacaccctgt ataaccagag gctgaagggc cgggccaccc tgaccgtgga taagagcatc  300
agcaccgctt atatggagct gtcccggctg cggtccgacg acaccgctgt gtattactgc  360
ggcaggtccg gcgtgtccgg cctggattac tggggccagg gcaccctggt gaccgtgagc  420
agcgctagca ccaagggacc ttctgtgttc cctctggctc cttcttctaa gtccacttcc  480
ggtggtacag cagctctggg ttgtctggtg aaggattact cccagaacc agtgactgtg  540
tcctggaact ccgagctct gacttctgga gtgcatactt tcccagcagt gctgcaatct  600
agcggactgt actctctgtc ttccgtggtg actgtgcctt cttcttccct ggggactcaa  660
acttacatct gcaacgtgaa ccacaagccc tccaacacca aggtggacaa gaaggtggag  720
ccaaagagct gcgataagac ccacacctgt ccaccttgtc cagctccaga actgctgggt  780
gggccttctg tgtttctgtt cccacctaag ccaaaggata ccctgatgat ctctaggacc  840
ccagaagtga cctgtgtggt cgtcgatgtg tctcatgaag accctgaagt gaagttcaac  900
tggtacgtgg acggggtgga agtgcataac gcaaagacca gcccaggga gagcaatac    960
aactccacct acagggtggt ctccgtcctg acagtcctgc atcaggattg gctgaacggc  1020
aaggagtaca gtgcaaggt ctccaataaa gccctgcctg cccctatcga gaaaaccatt   1080
agcaaagcca aaggccagcc cagggagccc caggtctata cactgccccc cagcagggag  1140
```

-continued

```
gagatgacaa aaaatcaggt cagcctgaca tgcctggtca aaggctttta tcccagcgac  1200
attgccgtcg agtgggagtc caatggccag cccgagaata attataaaac aacacccccc  1260
gtcctggaca gcgacggcag cttttttctg tatagcaaac tgacagtcga taaaagcagg  1320
tggcagcagg gcaatgtctt ttcctgcagc gtcatgcacg aggccctgca caatcactat  1380
actcagaaaa gcctgagcct gtcccccggg aaatgagcgg ccgc              1424

SEQ ID NO: 22          moltype = DNA  length = 1424
FEATURE                Location/Qualifiers
source                 1..1424
                       mol_type = other DNA
                       organism = synthetic construct
SEQUENCE: 22
gaattcgccg ccaccatgaa gcacctgtgg tttttcctgc tgctggtggc cgctcctcgg  60
tgggtgctgt cccaggtgca gctggtgcag agcggcgccg aggtgaagaa gcctggcgct  120
tccgtgaagg tgtcctgtaa ggccagcggc tacagcttca ccgactactt tatgaactgg  180
gtgaggcagg ctcctggcca gggcctggag tggatcggca ggatcaaccc ctatagcggc  240
gacaccctgt acaatcagaa gctgcagggc cgggtgacca tgaccgtgga caagtccatc  300
agcaccgctt acatggagct gtcccggctg cggagcgacg ataccgctgt gtattactgc  360
ggccggtccg gcgtgagcgg cttggattat tggggccagg gcaccctggt gaccgtgagc  420
tccgctagca ccaagggacc ttctgtgttc cctctggctc cttcttctaa gtccacttcc  480
ggtggtacag cagctctggg ttgtctggtg aaggattact tcccagaacc agtgactgtg  540
tcctgaaact ccggagctct gacttctgga gtgcatactt cccagcagt gctgcaatct  600
agcggactgt actctctgtc ttccgtggtg actgtgcctt cttcttccct ggggactcaa  660
acttacatct gcaacgtgaa ccacaagccc tccaacacca aggtggacaa gaaggtggag  720
ccaaagagct gcgataagac ccacacctgt ccaccttgtc cagctccaga actgctgggt  780
gggccttctg tgtttctgtt cccacctaag ccaaaggata ccctgatgat ctctaggacc  840
ccagaagtga cctgtgtggt cgtcgatgtg tctcatgaag accctgaagt gaagttcaac  900
tggtacgtgg acgggtgga agtgcataac gcaaagacca gcccaggga agagcaaatc  960
aactccacct acagggtggt ctccgtcctg acagtcctgc atcaggattg gctgaacggc  1020
aaggagtaca agtgcaaggt ctccaataaa gccctgcctg cccctatcga gaaaaccatt  1080
agcaaagcca aaggccagcc cagggagccc caggtctata cactgccccc cagcagggag  1140
gagatgacaa aaaatcaggt cagcctgaca tgcctggtca aaggctttta tcccagcgac  1200
attgccgtcg agtgggagtc caatggccag cccgagaata attataaaac aacacccccc  1260
gtcctggaca gcgacggcag cttttttctg tatagcaaac tgacagtcga taaaagcagg  1320
tggcagcagg gcaatgtctt ttcctgcagc gtcatgcacg aggccctgca caatcactat  1380
actcagaaaa gcctgagcct gtcccccggg aaatgagcgg ccgc              1424

SEQ ID NO: 23          moltype = DNA  length = 1424
FEATURE                Location/Qualifiers
source                 1..1424
                       mol_type = other DNA
                       organism = synthetic construct
SEQUENCE: 23
gaattcgccg ccaccatgaa gcacctgtgg tttttcctgc tgctggtggc cgccccccgg  60
tgggtgctgt cccaggtgca gctgcaggag agcggccctg gcctggtgaa gcccagcgag  120
accctgagcc tgacctgcac cgcttccggc tacagcttca ccgattactt catgaactgg  180
gtgcggcagc cccctggcaa gggcttggag tggatcggcc ggatcaaccc ttacagcggc  240
gacaccctgt ataatcagcg gctgaagggc agggtgaccc tgagcgtgga taagagcaag  300
aaccaggcca gcctgaagct gagcagcgtg accgctgccg ataccgccgt gtattattgt  360
ggccggtccg gcgtgagcgg cctggattac tggggccagg gcaccctggt gaccgtgagc  420
agcgctagca ccaagggacc ttctgtgttc cctctggctc cttcttctaa gtccacttcc  480
ggtggtacag cagctctggg ttgtctggtg aaggattact tcccagaacc agtgactgtg  540
tcctggaact ccggagctct gacttctgga gtgcatactt cccagcagt gctgcaatct  600
agcggactgt actctctgtc ttccgtggtg actgtgcctt cttcttccct ggggactcaa  660
acttacatct gcaacgtgaa ccacaagccc tccaacacca aggtggacaa gaaggtggag  720
ccaaagagct gcgataagac ccacacctgt ccaccttgtc cagctccaga actgctgggt  780
gggccttctg tgtttctgtt cccacctaag ccaaaggata ccctgatgat ctctaggacc  840
ccagaagtga cctgtgtggt cgtcgatgtg tctcatgaag accctgaagt gaagttcaac  900
tggtacgtgg acgggtgga agtgcataac gcaaagacca gcccaggga agagcaaatc  960
aactccacct acagggtggt ctccgtcctg acagtcctgc atcaggattg gctgaacggc  1020
aaggagtaca agtgcaaggt ctccaataaa gccctgcctg cccctatcga gaaaaccatt  1080
agcaaagcca aaggccagcc cagggagccc caggtctata cactgccccc cagcagggag  1140
gagatgacaa aaaatcaggt cagcctgaca tgcctggtca aaggctttta tcccagcgac  1200
attgccgtcg agtgggagtc caatggccag cccgagaata attataaaac aacacccccc  1260
gtcctggaca gcgacggcag cttttttctg tatagcaaac tgacagtcga taaaagcagg  1320
tggcagcagg gcaatgtctt ttcctgcagc gtcatgcacg aggccctgca caatcactat  1380
actcagaaaa gcctgagcct gtcccccggg aaatgagcgg ccgc              1424

SEQ ID NO: 24          moltype = DNA  length = 1424
FEATURE                Location/Qualifiers
source                 1..1424
                       mol_type = other DNA
                       organism = synthetic construct
SEQUENCE: 24
gaattcgccg ccaccatgaa gcacctgtgg tttttcctgc tgctggtggc tgctcctcgg  60
tgggtgctga gccaggtgca gctgcaggag agcggccccg gactggtgaa gcctagcgag  120
accctgtccc tgacctgcac cgccagcggc tattccttta ccgattattt catgaactgg  180
atccggcagc ccccctggcaa gggcctggag tggatcggcc ggatcaaccc ctattccggc  240
gataccctgt acaaccagcg gctgaagtcc agggtgaccc tgagcgtgga caagtccaag  300
```

-continued

```
aaccaggctt ccctgaagct gtccagcgtg accgctgctg ataccgctgt gtactactgc    360
ggccggagcg gcgtgtccgg cttggattat tggggccagg gcaccctggt gaccgtgagc    420
agcgctagca ccaagggacc ttctgtgttc cctctggctc cttcttctaa gtccacttcc    480
ggtggtacag cagctctggg ttgtctggtg aaggattact tcccagaacc agtgactgtg    540
tcctggaact ccggagctct gacttctgga gtgcatactt tcccagcagt gctgcaatct    600
agcggactgt actctctgtc ttccgtggtg actgtgcctt cttcttccct ggggactcaa    660
acttacatct gcaacgtgaa ccacaagccc tccaacacca aggtggacaa gaaggtggag    720
ccaaagagct gcgataagac ccacacctgt ccaccttgtc cagctccaga actgctgggt    780
gggccttctg tgtttctgtt cccacctaag ccaaaggata ccctgatgat ctctaggacc    840
ccagaagtga cctgtgtggt cgtcgatgtg tctcatgaag accctgaagt gaagttcaac    900
tggtacgtgg acggggtgga agtgcataac gcaaagacca gcccaggga agagcaatac     960
aactccacct acagggtggt ctccgtcctg acagtcctgc atcaggattg gctgaacggc   1020
aaggagtaca agtgcaaggt ctccaataaa gccctgcctg cccctatcga gaaaaccatt   1080
agcaaagcca aaggccagcc cagggagccc caggtctata cactgccccc cagcagggag   1140
gagatgacaa aaaatcaggt cagcctgaca tgcctggtca aaggcttttta tcccagcgac   1200
attgccgtcg agtgggagtc caatggccag cccgagaata attataaaac aacacccccc   1260
gtcctggaca gcgacggcag cttttttctg tatagcaaac tgacagtcga taaaagcagg   1320
tggcagcagg gcaatgtctt ttcctgcagc gtcatgcacg aggccctgca caatcactat   1380
actcagaaaa gcctgagcct gtcccccggg aaatgagcgg ccgc                     1424

SEQ ID NO: 25          moltype = DNA  length = 1424
FEATURE                Location/Qualifiers
source                 1..1424
                       mol_type = other DNA
                       organism = synthetic construct
SEQUENCE: 25
gaattcgccg ccaccatgaa gcacctgtgg ttctttctgc tgctggtggc cgcccccagg     60
tgggttctga gccaggtgca gctgcaggag agcggccccg gactggtgaa gcctagcgag    120
accctgtccc tgacctgcac cgtgtccggc ggctccatca ccgattattt catgaactgg    180
atcaggcagc cccctggcaa gggcctggag tggatcggca gatcaatcc ctatagcggc     240
gacaccctgt acaatcagcg gctgaagagc agggtgaccc tgagcgtgga taagtccaag    300
aatcaggcca gcctgaagct gtcctccgtg accgccgccg acaccgctgt gtactactgc    360
ggccggtccg gcgtgagcgg cttggattac tggggccagg gcaccctggt gaccgtgtcc    420
agcgctagca ccaagggacc ttctgtgttc cctctggctc cttcttctaa gtccacttcc    480
ggtggtacag cagctctggg ttgtctggtg aaggattact tcccagaacc agtgactgtg    540
tcctggaact ccggagctct gacttctgga gtgcatactt tcccagcagt gctgcaatct    600
agcggactgt actctctgtc ttccgtggtg actgtgcctt cttcttccct ggggactcaa    660
acttacatct gcaacgtgaa ccacaagccc tccaacacca aggtggacaa gaaggtggag    720
ccaaagagct gcgataagac ccacacctgt ccaccttgtc cagctccaga actgctgggt    780
gggccttctg tgtttctgtt cccacctaag ccaaaggata ccctgatgat ctctaggacc    840
ccagaagtga cctgtgtggt cgtcgatgtg tctcatgaag accctgaagt gaagttcaac    900
tggtacgtgg acggggtgga agtgcataac gcaaagacca gcccaggga agagcaatac     960
aactccacct acagggtggt ctccgtcctg acagtcctgc atcaggattg gctgaacggc   1020
aaggagtaca agtgcaaggt ctccaataaa gccctgcctg cccctatcga gaaaaccatt   1080
agcaaagcca aaggccagcc cagggagccc caggtctata cactgccccc cagcagggag   1140
gagatgacaa aaaatcaggt cagcctgaca tgcctggtca aaggcttttta tcccagcgac   1200
attgccgtcg agtgggagtc caatggccag cccgagaata attataaaac aacacccccc   1260
gtcctggaca gcgacggcag cttttttctg tatagcaaac tgacagtcga taaaagcagg   1320
tggcagcagg gcaatgtctt ttcctgcagc gtcatgcacg aggccctgca caatcactat   1380
actcagaaaa gcctgagcct gtcccccggg aaatgagcgg ccgc                     1424

SEQ ID NO: 26          moltype = DNA  length = 1424
FEATURE                Location/Qualifiers
source                 1..1424
                       mol_type = other DNA
                       organism = synthetic construct
SEQUENCE: 26
gaattcgccg ccaccatgaa gcacctgtgg ttcttcctgc tgctggtggc tgctcctagg     60
tgggtgctga gcgaggtgca gctggtgcag agcggcgccg aggtgaagaa gcccggcgag    120
agcctgaaga tctcctgtaa ggcttccggc tactccttca ccgactactt tatgaattgg    180
gtgcggcaga tgcccggcaa gggccggag tggatcggca gaatcaatcc ttacagcggc     240
gacaccctgt acaaccagcg gctgcagggc caggtgaccc tgtccgctga taagagcatc    300
tccaccgcct acctgcagct gtcctccctg aaggcctccg acaccgccat gtactactgt    360
ggcaggagcg gcgtgagcgg cctggactac tggggccagg gcaccctggt gaccgtgagc    420
agcgctagca ccaagggacc ttctgtgttc cctctggctc cttcttctaa gtccacttcc    480
ggtggtacag cagctctggg ttgtctggtg aaggattact tcccagaacc agtgactgtg    540
tcctggaact ccggagctct gacttctgga gtgcatactt tcccagcagt gctgcaatct    600
agcggactgt actctctgtc ttccgtggtg actgtgcctt cttcttccct ggggactcaa    660
acttacatct gcaacgtgaa ccacaagccc tccaacacca aggtggacaa gaaggtggag    720
ccaaagagct gcgataagac ccacacctgt ccaccttgtc cagctccaga actgctgggt    780
gggccttctg tgtttctgtt cccacctaag ccaaaggata ccctgatgat ctctaggacc    840
ccagaagtga cctgtgtggt cgtcgatgtg tctcatgaag accctgaagt gaagttcaac    900
tggtacgtgg acggggtgga agtgcataac gcaaagacca gcccaggga agagcaatac     960
aactccacct acagggtggt ctccgtcctg acagtcctgc atcaggattg gctgaacggc   1020
aaggagtaca agtgcaaggt ctccaataaa gccctgcctg cccctatcga gaaaaccatt   1080
agcaaagcca aaggccagcc cagggagccc caggtctata cactgccccc cagcagggag   1140
gagatgacaa aaaatcaggt cagcctgaca tgcctggtca aaggcttttta tcccagcgac   1200
attgccgtcg agtgggagtc caatggccag cccgagaata attataaaac aacacccccc   1260
gtcctggaca gcgacggcag cttttttctg tatagcaaac tgacagtcga taaaagcagg   1320
```

-continued

```
tggcagcagg gcaatgtctt ttcctgcagc gtcatgcacg aggccctgca caatcactat   1380
actcagaaaa gcctgagcct gtcccccggg aaatgagcgg ccgc                    1424

SEQ ID NO: 27          moltype = DNA   length = 725
FEATURE                Location/Qualifiers
source                 1..725
                       mol_type = other DNA
                       organism = synthetic construct
SEQUENCE: 27
gaattcgccg ccaccatggt gctgcagacc caggtgttta tctccctgct gctgtggatc     60
agcggcgcct atggcgagat cgtgctgacc cagtcccctg atttccagag cgtgacccct    120
aaggagaagc tgaccatcac ctgcagcgcc agcagctccg ccagctatat gcactggtac    180
cagcagaagc ccgaccagtc ccctaagcgg tggatctatg acaccagcaa gctggctagc    240
ggcgtgccta gcaggttctc cggcagcggc agcggcacag actacaccct gaccatcaac    300
tccctggagg ctgaggacgc cgccacctat tactgccagc agtggagctc caacccccct    360
acctttggcg gcggcaccaa ggtggagatc aagcgtacgg tggctgcacc ttctgtgttc    420
atcttccctc catctgatga gcagctgaag tctggaaccg catctgtcgt ctgtctgctg    480
aacaacttt accccaggga ggctaaggtc caatggaagg tggacaacgc cctgcagtct     540
ggtaatagcc aggaaagcgt gaccgaacag gattccaagg actccaccta ctccctgtcc    600
tccacactga cactgagcaa agccgactat gaaaagcaca aagtgtatgc ctgcgaggtc    660
actcatcagg gcctgtccag ccccgtgact aaaagcttta atagggggga gtgctgagcg    720
gccgc                                                               725

SEQ ID NO: 28          moltype = DNA   length = 725
FEATURE                Location/Qualifiers
source                 1..725
                       mol_type = other DNA
                       organism = synthetic construct
SEQUENCE: 28
gaattcgccg ccaccatggt gctgcagacc caggtgttta tcagcctgct gctgtggatc     60
agcggcgcct acggcgagat cgtgctgacc cagtcccccg ccaccctgtc cctgtcccca    120
ggagagaggg ctaccctgag ctgctccgcc agctccagcg cctcctacat ccactggtac    180
cagcagaagc tggccaggc ccctcggaga tggatgtacg atacctccaa gctggcctcc     240
ggcatccccg ccagattcag cggcagcggc agcggaaccg attacaccct gaccatcagc    300
tccctggagg ctgaggacgc cgccgtgtac tactgccagc agtggagcag caacccctcc    360
accttcggcg gcggcaccaa ggtggagatc aagcgtacgg tggctgcacc ttctgtgttc    420
atcttccctc catctgatga gcagctgaag tctggaaccg catctgtcgt ctgtctgctg    480
aacaacttt accccaggga ggctaaggtc caatggaagg tggacaacgc cctgcagtct     540
ggtaatagcc aggaaagcgt gaccgaacag gattccaagg actccaccta ctccctgtcc    600
tccacactga cactgagcaa agccgactat gaaaagcaca aagtgtatgc ctgcgaggtc    660
actcatcagg gcctgtccag ccccgtgact aaaagcttta atagggggga gtgctgagcg    720
gccgc                                                               725

SEQ ID NO: 29          moltype = DNA   length = 725
FEATURE                Location/Qualifiers
source                 1..725
                       mol_type = other DNA
                       organism = synthetic construct
SEQUENCE: 29
gaattcgccg ccaccatggt gctgcagacc caggtgttta tcagcctgct gctgtggatc     60
agcggcgctt acggcgacat ccagctgacc cagtcccccc ccagcctgag cgctagcgtg    120
ggcgaccggg tgaccatcac ctgctccgcc tccagctccg ccagctacat gcactggtac    180
cagcagaagc ccggcaaggc ccccaagaac tggatctatg ataccagcaa gctggccagc    240
ggcgtgccca gcagattcag cggcagcggc tccggcaccg attacaccct gaccatcagc    300
tccctgcagc ccgaggatgc tgccacctac tactgccagc agtggtcctc caacccccct    360
acctttggcg gcggcaccaa ggtggagatc aagcgtacgg tggctgcacc ttctgtgttc    420
atcttccctc catctgatga gcagctgaag tctggaaccg catctgtcgt ctgtctgctg    480
aacaacttt accccaggga ggctaaggtc caatggaagg tggacaacgc cctgcagtct     540
ggtaatagcc aggaaagcgt gaccgaacag gattccaagg actccaccta ctccctgtcc    600
tccacactga cactgagcaa agccgactat gaaaagcaca aagtgtatgc ctgcgaggtc    660
actcatcagg gcctgtccag ccccgtgact aaaagcttta atagggggga gtgctgagcg    720
gccgc                                                               725

SEQ ID NO: 30          moltype = AA   length = 466
FEATURE                Location/Qualifiers
source                 1..466
                       mol_type = protein
                       organism = synthetic construct
SEQUENCE: 30
MKHLWFFLLL VAAPRWVLSQ VQLVQSGAEV KKPGASVKVS CKASGYSFTD YFMNWVRQAP     60
GQGLEWIGRI NPYSGDTLYN QRLKGRATLT VDKSISTAYM ELSRLRSDDT AVYYCGRSGV    120
SGLDYWGQGT LVTVSSASTK GPSVFPLAPS SKSTSGGTAA LGCLVKDYFP EPVTVSWNSG    180
ALTSGVHTFP AVLQSSGLYS LSSVVTVPSS SLGTQTYICN VNHKPSNTKV DKKVEPKSCD    240
KTHTCPPCPA PELLGGPSVF LFPPKPKDTL MISRTPEVTC VVVDVSHEDP EVKFNWYVDG    300
VEVHNAKTKP REEQYNSTYR VVSVLTVLHQ DWLNGKEYKC KVSNKALPAP IEKTISKAKG    360
QPREPQVYTL PPSREEMTKN QVSLTCLVKG FYPSDIAVEW ESNGQPENNY KTTPPVLDSD    420
GSFFLYSKLT VDKSRWQQGN VFSCSVMHEA LHNHYTQKSL SLSPGK                   466

SEQ ID NO: 31          moltype = AA   length = 466
```

```
FEATURE                    Location/Qualifiers
source                     1..466
                           mol_type = protein
                           organism = synthetic construct
SEQUENCE: 31
MKHLWFFLLL VAAPRWVLSQ VQLVQSGAEV KKPGASVKVS CKASGYSFTD YFMNWVRQAP    60
GQGLEWIGRI NPYSGDTLYN QKLQGRVTMT VDKSISTAYM ELSRLRSDDT AVYYCGRSGV   120
SGLDYWGQGT LVTVSSASTK GPSVFPLAPS SKSTSGGTAA LGCLVKDYFP EPVTVSWNSG   180
ALTSGVHTFP AVLQSSGLYS LSSVVTVPSS SLGTQTYICN VNHKPSNTKV DKKVEPKSCD   240
KTHTCPPCPA PELLGGPSVF LFPPKPKDTL MISRTPEVTC VVVDVSHEDP EVKFNWYVDG   300
VEVHNAKTKP REEQYNSTYR VVSVLTVLHQ DWLNGKEYKC KVSNKALPAP IEKTISKAKG   360
QPREPQVYTL PPSREEMTKN QVSLTCLVKG FYPSDIAVEW ESNGQPENNY KTTPPVLDSD   420
GSFFLYSKLT VDKSRWQQGN VFSCSVMHEA LHNHYTQKSL SLSPGK               466

SEQ ID NO: 32              moltype = AA   length = 466
FEATURE                    Location/Qualifiers
source                     1..466
                           mol_type = protein
                           organism = synthetic construct
SEQUENCE: 32
MKHLWFFLLL VAAPRWVLSQ VQLQESGPGL VKPSETLSLT CTASGYSFTD YFMNWVRQPP    60
GKGLEWIGRI NPYSGDTLYN QRLKGRVTLS VDKSKNQASL KLSSVTAADT AVYYCGRSGV   120
SGLDYWGQGT LVTVSSASTK GPSVFPLAPS SKSTSGGTAA LGCLVKDYFP EPVTVSWNSG   180
ALTSGVHTFP AVLQSSGLYS LSSVVTVPSS SLGTQTYICN VNHKPSNTKV DKKVEPKSCD   240
KTHTCPPCPA PELLGGPSVF LFPPKPKDTL MISRTPEVTC VVVDVSHEDP EVKFNWYVDG   300
VEVHNAKTKP REEQYNSTYR VVSVLTVLHQ DWLNGKEYKC KVSNKALPAP IEKTISKAKG   360
QPREPQVYTL PPSREEMTKN QVSLTCLVKG FYPSDIAVEW ESNGQPENNY KTTPPVLDSD   420
GSFFLYSKLT VDKSRWQQGN VFSCSVMHEA LHNHYTQKSL SLSPGK               466

SEQ ID NO: 33              moltype = AA   length = 466
FEATURE                    Location/Qualifiers
source                     1..466
                           mol_type = protein
                           organism = synthetic construct
SEQUENCE: 33
MKHLWFFLLL VAAPRWVLSQ VQLQESGPGL VKPSETLSLT CTASGYSFTD YFMNWIRQPP    60
GKGLEWIGRI NPYSGDTLYN QRLKSRVTLS VDKSKNQASL KLSSVTAADT AVYYCGRSGV   120
SGLDYWGQGT LVTVSSASTK GPSVFPLAPS SKSTSGGTAA LGCLVKDYFP EPVTVSWNSG   180
ALTSGVHTFP AVLQSSGLYS LSSVVTVPSS SLGTQTYICN VNHKPSNTKV DKKVEPKSCD   240
KTHTCPPCPA PELLGGPSVF LFPPKPKDTL MISRTPEVTC VVVDVSHEDP EVKFNWYVDG   300
VEVHNAKTKP REEQYNSTYR VVSVLTVLHQ DWLNGKEYKC KVSNKALPAP IEKTISKAKG   360
QPREPQVYTL PPSREEMTKN QVSLTCLVKG FYPSDIAVEW ESNGQPENNY KTTPPVLDSD   420
GSFFLYSKLT VDKSRWQQGN VFSCSVMHEA LHNHYTQKSL SLSPGK               466

SEQ ID NO: 34              moltype = AA   length = 466
FEATURE                    Location/Qualifiers
source                     1..466
                           mol_type = protein
                           organism = synthetic construct
SEQUENCE: 34
MKHLWFFLLL VAAPRWVLSQ VQLQESGPGL VKPSETLSLT CTVSGGSITD YFMNWIRQPP    60
GKGLEWIGRI NPYSGDTLYN QRLKSRVTLS VDKSKNQASL KLSSVTAADT AVYYCGRSGV   120
SGLDYWGQGT LVTVSSASTK GPSVFPLAPS SKSTSGGTAA LGCLVKDYFP EPVTVSWNSG   180
ALTSGVHTFP AVLQSSGLYS LSSVVTVPSS SLGTQTYICN VNHKPSNTKV DKKVEPKSCD   240
KTHTCPPCPA PELLGGPSVF LFPPKPKDTL MISRTPEVTC VVVDVSHEDP EVKFNWYVDG   300
VEVHNAKTKP REEQYNSTYR VVSVLTVLHQ DWLNGKEYKC KVSNKALPAP IEKTISKAKG   360
QPREPQVYTL PPSREEMTKN QVSLTCLVKG FYPSDIAVEW ESNGQPENNY KTTPPVLDSD   420
GSFFLYSKLT VDKSRWQQGN VFSCSVMHEA LHNHYTQKSL SLSPGK               466

SEQ ID NO: 35              moltype = AA   length = 466
FEATURE                    Location/Qualifiers
source                     1..466
                           mol_type = protein
                           organism = synthetic construct
SEQUENCE: 35
MKHLWFFLLL VAAPRWVLSE VQLVQSGAEV KKPGESLKIS CKASGYSFTD YFMNWVRQMP    60
GKGLEWIGRI NPYSGDTLYN QRLQGQVTLS ADKSISTAYL QLSSLKASDT AMYYCGRSGV   120
SGLDYWGQGT LVTVSSASTK GPSVFPLAPS SKSTSGGTAA LGCLVKDYFP EPVTVSWNSG   180
ALTSGVHTFP AVLQSSGLYS LSSVVTVPSS SLGTQTYICN VNHKPSNTKV DKKVEPKSCD   240
KTHTCPPCPA PELLGGPSVF LFPPKPKDTL MISRTPEVTC VVVDVSHEDP EVKFNWYVDG   300
VEVHNAKTKP REEQYNSTYR VVSVLTVLHQ DWLNGKEYKC KVSNKALPAP IEKTISKAKG   360
QPREPQVYTL PPSREEMTKN QVSLTCLVKG FYPSDIAVEW ESNGQPENNY KTTPPVLDSD   420
GSFFLYSKLT VDKSRWQQGN VFSCSVMHEA LHNHYTQKSL SLSPGK               466

SEQ ID NO: 36              moltype = AA   length = 233
FEATURE                    Location/Qualifiers
source                     1..233
                           mol_type = protein
                           organism = synthetic construct
```

-continued

```
SEQUENCE: 36
MVLQTQVFIS LLLWISGAYG EIVLTQSPDF QSVTPKEKVT ITCSASSSAS YMHWYQQKPD    60
QSPKRWIYDT SKLASGVPSR FSGSGSGTDY TLTINSLEAE DAATYYCQQW SSNPPTFGGG    120
TKVEIKRTVA APSVFIFPPS DEQLKSGTAS VVCLLNNFYP REAKVQWKVD NALQSGNSQE    180
SVTEQDSKDS TYSLSSTLTL SKADYEKHKV YACEVTHQGL SSPVTKSFNR GEC          233

SEQ ID NO: 37             moltype = AA  length = 232
FEATURE                   Location/Qualifiers
source                    1..232
                          mol_type = protein
                          organism = synthetic construct
SEQUENCE: 37
MVLQTQVFIS LLLWISGAYG EIVLTQSPAT LSLSPGERAT LSCSASSSAS YIHWYQQKPG    60
QAPRRWMYDT SKLASGIPAR FSGSGSGTDY TLTISSLEPE DAAVYYCQQW SSNPPTFGGG    120
TKVEIKRTVA APSVFIFPPS DEQLKSGTAS VVCLLNNFYP REAKVQWKVD NALQSGNSQE    180
SVTEQDSKDS TYSLSSTLTL SKADYEKHKV YACEVTHQGL SSPVTKSFNR GE           232

SEQ ID NO: 38             moltype = AA  length = 233
FEATURE                   Location/Qualifiers
source                    1..233
                          mol_type = protein
                          organism = synthetic construct
SEQUENCE: 38
MVLQTQVFIS LLLWISGAYG DIQLTQSPSS LSASVGDRVT ITCSASSSAS YMHWYQQKPG    60
KAPKNWIYDT SKLASGVPSR FSGSGSGTDY TLTISSLQPE DAATYYCQQW SSNPPTFGGG    120
TKVEIKRTVA APSVFIFPPS DEQLKSGTAS VVCLLNNFYP REAKVQWKVD NALQSGNSQE    180
SVTEQDSKDS TYSLSSTLTL SKADYEKHKV YACEVTHQGL SSPVTKSFNR GEC          233
```